(12) United States Patent
Najarian et al.

(10) Patent No.: US 11,615,527 B2
(45) Date of Patent: Mar. 28, 2023

(54) AUTOMATED ANATOMIC AND REGIONAL LOCATION OF DISEASE FEATURES IN COLONOSCOPY VIDEOS

(71) Applicant: THE REGENTS OF THE UNIVERSITY OF MICHIGAN, Ann Arbor, MI (US)

(72) Inventors: Kayvan Najarian, Ann Arbor, MI (US); Heming Yao, Ann Arbor, MI (US); Sayedmohammadreza Soroushmehr, Ann Arbor, MI (US); Jonathan Gryak, Ann Arbor, MI (US); Ryan W. Stidham, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 424 days.

(21) Appl. No.: 16/875,357

(22) Filed: May 15, 2020

(65) Prior Publication Data
US 2020/0364859 A1 Nov. 19, 2020

Related U.S. Application Data

(60) Provisional application No. 62/848,724, filed on May 16, 2019.

(51) Int. Cl.
*G06K 9/00* (2022.01)
*G06T 7/00* (2017.01)
(Continued)

(52) U.S. Cl.
CPC .......... *G06T 7/0012* (2013.01); *G06F 16/285* (2019.01); *G06K 9/6284* (2013.01);
(Continued)

(58) Field of Classification Search
None
See application file for complete search history.

(56) References Cited

U.S. PATENT DOCUMENTS

| 10,733,745 | B2 * | 8/2020 | Pizer | ........................ G06T 19/20 |
| 2008/0058593 | A1 | 3/2008 | Gu et al. | |

(Continued)

OTHER PUBLICATIONS

Liu et al., "An optical flow approach to tracking colonoscopy video", Computerized Medical Imaging and Graphics 37 (2013) 207-223 (Year: 2013).*

(Continued)

*Primary Examiner* — Soo Jin Park
(74) *Attorney, Agent, or Firm* — Harness, Dickey & Pierce, P.L.C.

(57) ABSTRACT

A system for automatically analyzing a video recording of a colonoscopy includes a processor and memory storing instructions, which when executed by the processor, cause the processor to receive the video recording of the colonoscopy performed on the colon and detect informative frames in the video recording. A frame is informative if the clarity of the frame is above a threshold or if the frame includes clinically relevant information about the colon. The instructions cause the processor to generate scores indicating severity levels of a disease for a plurality of the informative frames, estimate locations of the plurality of the informative frames in the colon, and generate an output indicating a distribution of the scores over one or more segments of the colon by combining the scores generated for the plurality of the informative frames and the estimated locations of the plurality of the informative frames in the colon.

51 Claims, 13 Drawing Sheets

(51) Int. Cl.
    *G06K 9/62*       (2022.01)
    *G06T 7/269*     (2017.01)
    *G06T 7/73*       (2017.01)
    *G06T 7/50*       (2017.01)
    *G06N 3/08*       (2023.01)
    *G16H 30/20*     (2018.01)
    *G06F 16/28*     (2019.01)

(52) U.S. Cl.
    CPC ............... *G06N 3/08* (2013.01); *G06T 7/269* (2017.01); *G06T 7/50* (2017.01); *G06T 7/73* (2017.01); *G16H 30/20* (2018.01); *G06T 2207/10016* (2013.01); *G06T 2207/10024* (2013.01); *G06T 2207/20081* (2013.01); *G06T 2207/20084* (2013.01); *G06T 2207/30028* (2013.01); *G06T 2207/30244* (2013.01)

(56) References Cited

U.S. PATENT DOCUMENTS

| | | |
|---|---|---|
| 2018/0075599 A1 | 3/2018 | Tajbakhsh et al. |
| 2018/0225820 A1 | 8/2018 | Liang et al. |
| 2018/0296281 A1 | 10/2018 | Yeung et al. |
| 2019/0080454 A1 | 3/2019 | Hameed et al. |

OTHER PUBLICATIONS

Zhang et al., "Polyp detection during colonoscopy using a regression-based convolutional neural network with a tracker", Nov. 2018, retrieved on [Sep. 11, 2020]. Retrieved from the internet <URL: https://www.ncbi.nim.nih.gov/pmc/articles/PMC6519928/pdf/nihms-1027305.pdf>, entire document.

* cited by examiner

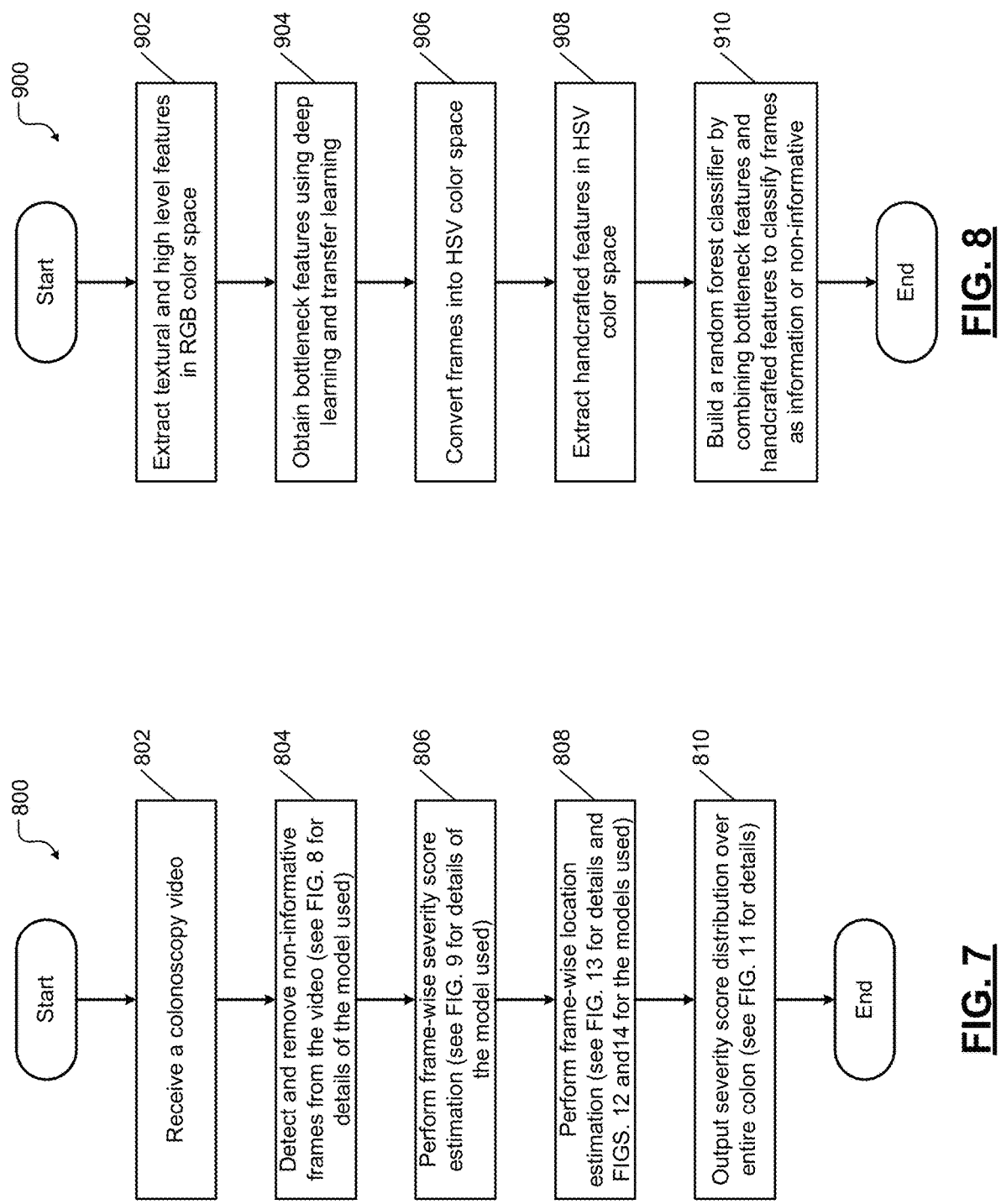

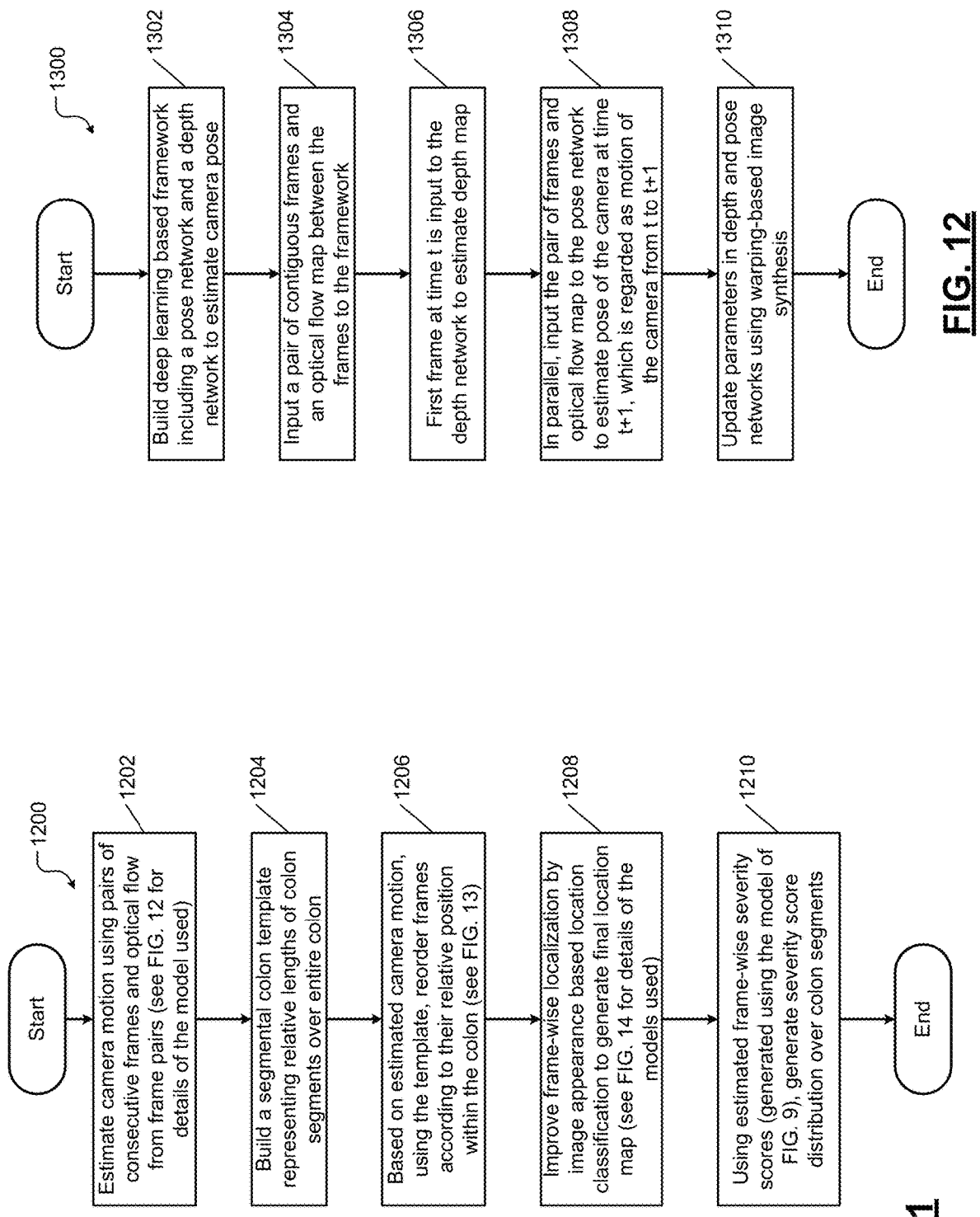

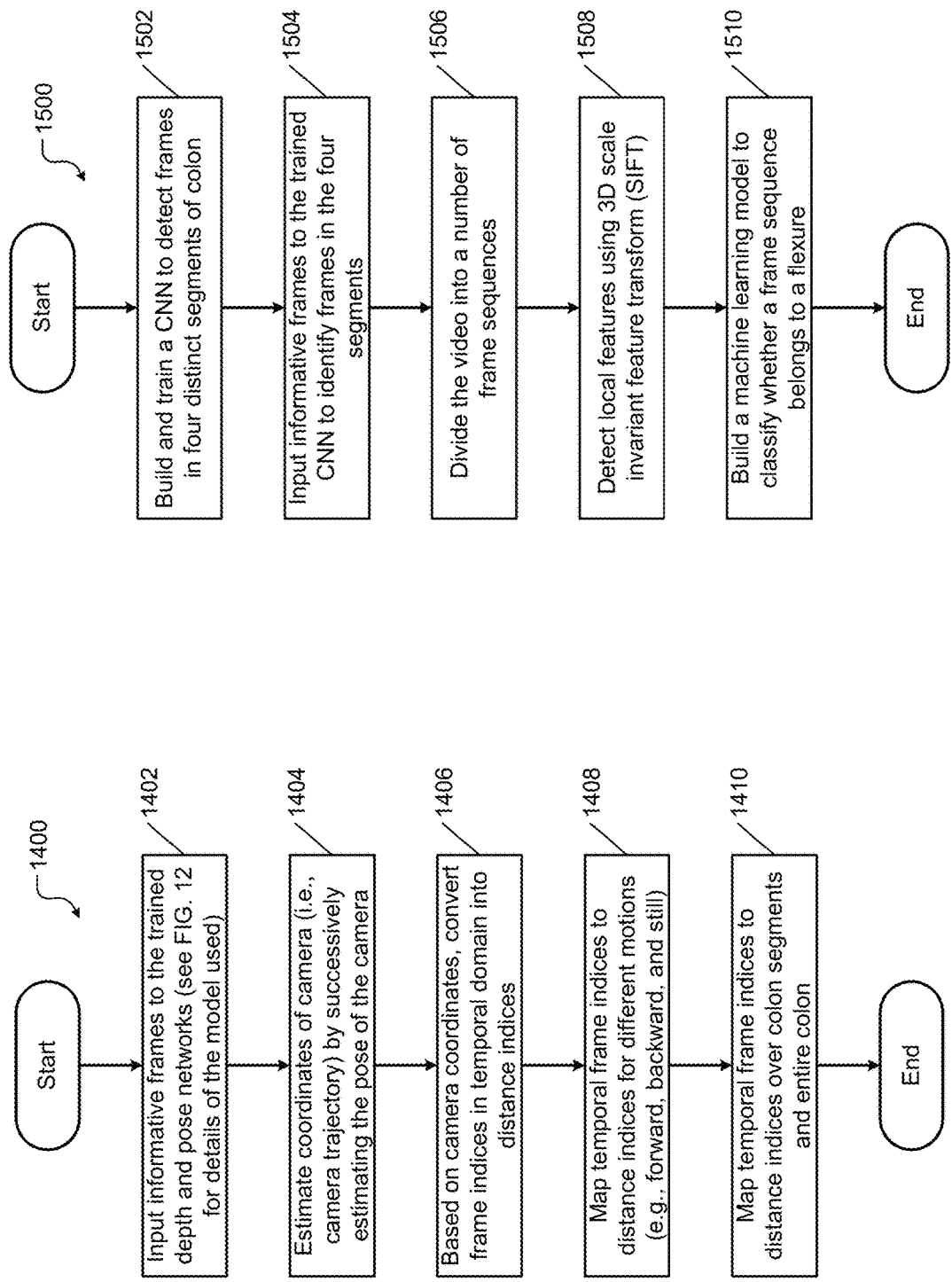

AUTOMATED ANATOMIC AND REGIONAL LOCATION OF DISEASE FEATURES IN COLONOSCOPY VIDEOS

CROSS-REFERENCE TO RELATED APPLICATION

This application claims the benefit of U.S. Provisional Application No. 62/848,724, filed on May 16, 2019. The entire disclosure of the above application is incorporated herein by reference.

FIELD

The present disclosure relates to automated anatomic and regional location of disease features in colonoscopy videos.

BACKGROUND

This section provides background information related to the present disclosure which is not necessarily prior art.

Colonoscopy is commonly performed to inspect the colon surface for a range of abnormalities such as polyps, adenocarcinoma, diverticula, and inflammatory changes in the colon. Optical colonoscopy is a medical procedure where a flexible probe containing a charge-coupled device (CCD) camera and a fiber optic light source is inserted into the rectum and advanced through the length of the colon. Often, a video recording of the procedure is later analyzed by gastroenterologists with specific disease expertise. This expert centralized review of videos is both time consuming and restricted to the limited number of expert reviewers available. Disease diagnosis, grading of disease severity, or risk assessment regarding the colonic disease is provided based on the review.

Although colonoscopy is commonly used in both diagnosis and longitudinal monitoring of disease activity for colorectal cancer and inflammatory bowel disease, objective grading of disease severity is challenging. First, disease severity features are qualitative in nature, such as the degree of erythema or redness, identifying edema or swelling, and the presence of erosions (very small ulcers) vs. frank ulceration. While several quantitative scores ca be generated to quantify these features, they are fundamentally qualitative. This results in inter-observer and intra-observer variation and limited reliability of scoring. Further, many evaluation systems only provide summary scores of the entire colon, attempting to compress all disease activity observed into a single score. Failure to efficiently account for the variable disease severity by location results in scores being variable and making the comparison of scores between individuals challenging.

An efficient computer-aided system to automatically analyze colonoscopy video recordings for automated detection and estimation of disease features could facilitate objective diagnosis and disease severity measurement, which would aid in treatment selection, the evaluation of therapeutic effect, and the clinical outcome prediction using standardized disease assessment.

SUMMARY

This section provides a general summary of the disclosure, and is not a comprehensive disclosure of its full scope or all of its features.

Systems for automatically analyzing a video recording of a colonoscopy are disclosed. Each of the systems comprises a processor and memory storing instructions for execution by the processor. In one embodiment, the instructions cause the processor to receive the video recording of the colonoscopy performed on the colon and detect informative frames in the video recording. A frame is informative if the clarity of the frame is above a threshold or if the frame includes clinically relevant information about the colon. The instructions cause the processor to generate scores indicating severity levels of a disease for a plurality of the informative frames, estimate locations of the plurality of the informative frames in the colon, and generate an output indicating a distribution of the scores over one or more segments of the colon by combining the scores generated for the plurality of the informative frames and the estimated locations of the plurality of the informative frames in the colon.

In another embodiment, the instructions cause the processor to receive the video recording of the colonoscopy performed on the colon, and extract features from frames of the video recording used for classifying frames as informative versus non-informative in Red-Green-Blue color space. The instructions cause the processor to input the features to a convolutional neural network, and receive, from the convolutional neural network, bottleneck features from the frames of the video recording in Red-Green-Blue color space. The instructions cause the processor to convert the frames of the video recording into Hue-Saturation-Value color space, and extract other features from the converted frames to identify non-informative frames and to distinguish the non-informative frames from the informative frames. A frame is informative if the clarity of the frame is above a threshold or if the frame includes clinically relevant information about the colon. The instructions cause the processor to generate a frame classification model using a combination of the bottleneck features and the other features to automatically identify the non-informative frames and output the informative frames.

In another embodiment, the instructions cause the processor to receive the video recording of the colonoscopy performed on the colon, and detect informative frames in the video recording. A frame is informative if the clarity of the frame is above a threshold or if the frame includes clinically relevant information about the colon. The instructions cause the processor to input the plurality of the informative frames to a convolutional neural network, and receive scores indicating severity levels of a disease for the plurality of the informative frames from the convolutional neural network.

In another embodiment, the instructions cause the processor to receive the video recording of the colonoscopy performed on the colon, and detect informative frames in the video recording. A frame is informative if the clarity of the frame is above a threshold or if the frame includes clinically relevant information about the colon. The instructions cause the processor to estimate locations of a plurality of the informative frames in the colon by estimating motion of a camera used to capture the video recording based on pairs of frames from the plurality of the informative frames and optical flow from the pairs of frames, generating a template representing relative lengths of segments of the colon, determining, using the template, relative positions of the plurality of the informative frames in the segments of the colon based on the estimated motion of the camera, and reordering the plurality of the informative frames according to the relative positions of the plurality of the informative frames in the segments of the colon.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 7 shows an overall method for automatically analyzing a colonoscopy video according to the present disclosure.

FIG. 8 shows a method for generating a model for automatically detecting informative and non-informative frames in a colonoscopy video according to the present disclosure.

FIG. 11 shows a method for automatically performing frame-wise location estimation for a colonoscopy video according to the present disclosure.

FIG. 12 shows a method for building a model for automatically estimating camera motion using pairs of consecutive frames and optical flow from the frame pairs of a colonoscopy video according to the present disclosure.

FIG. 13 shows a method for automatically mapping frames of a colonoscopy video to colon segments according to the present disclosure.

FIG. 14 shows a method for building models for providing image appearance-based location classification for frames of a colonoscopy video to generate a final location map according to the present disclosure.

Corresponding reference numerals indicate corresponding parts throughout the several views of the drawings.

DETAILED DESCRIPTION

Figure 1:
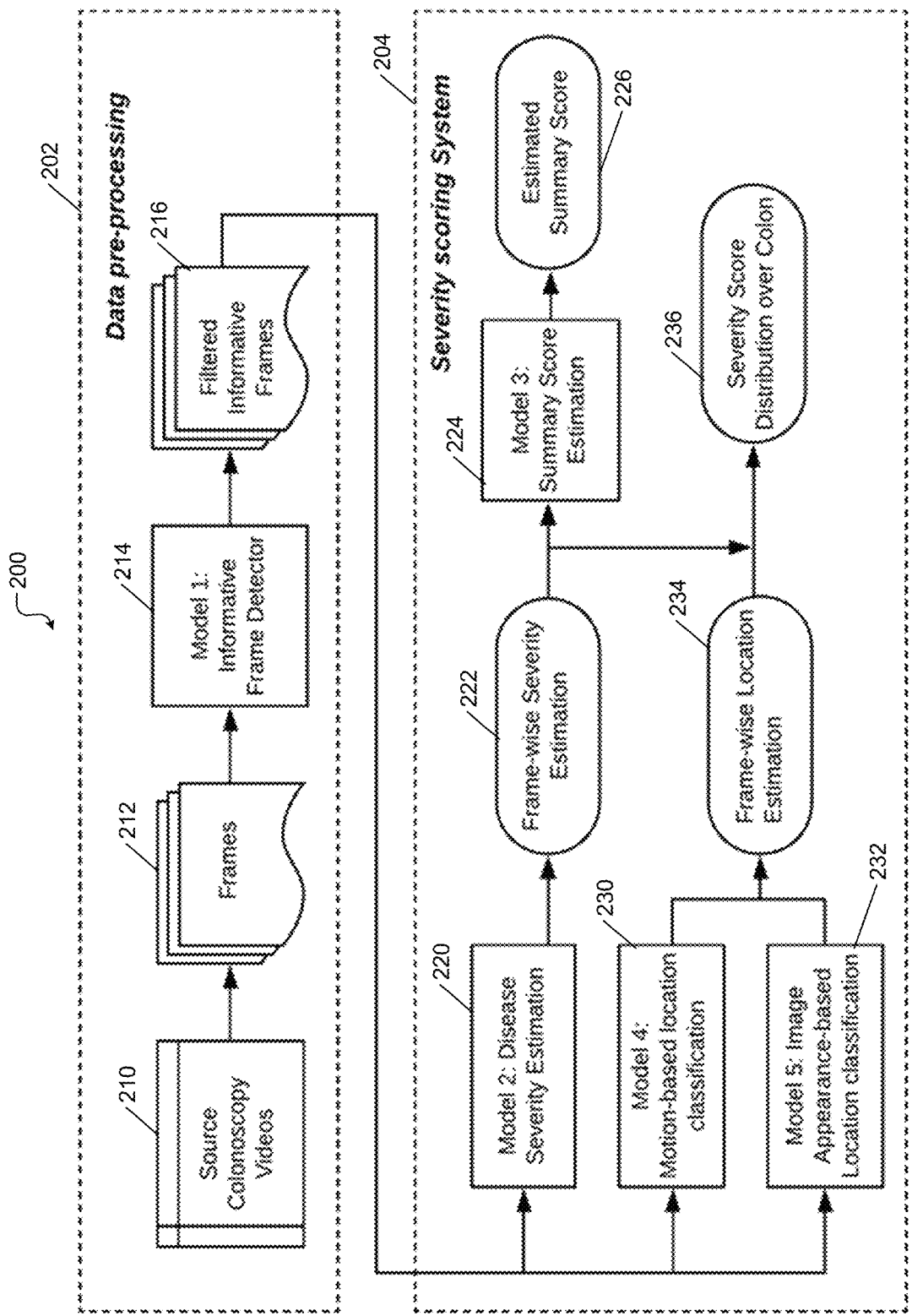
FIG. 1 shows an overall architecture of an automated video analysis system of the present disclosure.

Example embodiments will now be described more fully with reference to the accompanying drawings.

Colonoscopy is a common medical examination used to detect abnormalities in the colon. A broad range of disease findings is possible including structural abnormalities (e.g., diverticular disease), pre-cancerous and cancerous lesions, as well as acute and chronic inflammatory features (e.g., Crohn's disease, ulcerative colitis, and chronic infectious colitis). Despite its common use in both the diagnosis and longitudinal monitoring of disease, there are several problems related to the interpretation of colonoscopies by medical professionals, including the following: Subjective definitions of many disease features found on colonoscopy; Challenges in objectively grading (or scoring) the severity of disease features; and variability in the accuracy of reported localization of features.

These challenges can be addressed by using applications of computer-assisted methods to detect, identify, and grade colon disease findings using artificial intelligence techniques. Deep learning methods (e.g., convolutional neural networks) can be applied to medical imaging, including colonoscopy, for the detection and grading of disease severity with success. However, equally important for identifying the presence of a disease feature is the ability to localize the features. Disease finding localization would be of enormous benefit in conditions like Crohn's disease, ulcerative colitis, and other chronic gastro-intestinal illnesses where the distribution of disease severity is highly relevant. In addition, localization abilities would allow for the comparison of disease severity by region between serial examinations, a process even trained content experts cannot reliably perform. At present, there is no method for localization awareness using a traditional 2D recorded endoscopy.

The present disclosure proposes a computer-aided colonoscopy video analysis system that can assess locational awareness at the frame level and can be used to detect the regional location of findings in the colon. The system has broad applicability. For example, the system can be used to address the problem of delivering objective, reproducible, and regionally localized grading of ulcerative colitis. The ability to perform regional localization would be of high value for colorectal cancer screening, post-operative polyp surveillance, Barrett's esophagus, and other endoscopic diseases as well.

The colonoscopy lesion detection and regional localization system of the present disclosure comprises several interacting components: A non-informative frame detection component; A disease feature detection and disease severity estimation component; A colonic motion tracking and regional localization component; and Co-registration of disease finding/grading with colon localization information.

Broadly speaking, as explained below in detail, the present disclosure provides systems and methods for automatically analyzing colonoscopy videos using various trained models and numerous video processing and analysis schemes. Specifically, the systems and methods separate informative frames from the non-informative frames in the videos, perform frame-wise severity score estimation for the informative frames, perform location estimation of the informative frames relative to colon segments, and provide a distribution of severity scores throughout the colon based on the combination of the frame-wise severity score estimation and location estimation. Further, the location estimation is performed using camera motion analysis, which is improved by image appearance-based location classification. These and other aspects of the present disclosure are now explained below in detail.

The present disclosure is organized as follows. Initially, an overview of a video analysis system of the present disclosure is provided with reference to FIG. 1. The system is then described in detail with reference to FIGS. 2-6.

Various methods for analyzing the video according to the present disclosure are described in detail with reference to FIGS. 7-14. A distributed computing environment in which the systems and methods of the present disclosure can be implemented is described with reference to FIGS. 15-17.

While colonoscopy is used as an illustrative example throughout the present disclosure, the methods presented in this disclosure are not so limited. Rather, the methods of the present disclosure are applicable to many other non-surgical investigative procedures performed on human body such as, for example, upper endoscopy (esophagogastroduodenoscopy), endoscopic retrograde cholangiopancreatography (ERCP), cystoscopy and urologic procedures, and laparoscopic surgical procedures.

The video analysis system of the present disclosure is now described in greater detail with reference to FIGS. 1-6 with the following clarifications. While frame-wise severity and location estimation is described throughout the present disclosure to emphasize the capabilities of the systems and methods of the present disclosure, it may not be necessary to perform severity and location estimation for each informative frame. In some applications, it may suffice to perform severity and location estimation using fewer than all of the informative frames. For example, every alternate informative frame may suffice; selecting an informative frame after every N informative frames may suffice, where N is an integer greater than 1; and so on. Further, although the system can provide a severity score distribution over all of the colon segments (i.e., over the entire colon), the system can also be configured to provide a severity score distribution over a selected colon segment instead of all the colon segments. As used herein, the severity score distribution over a segment or segments of a colon indicates what are the severity scores along the length of a segment or segments of a colon, rather than indicating a single or a summary score for an entire segment or segments of a colon.

Further, the present disclosure describes various models and training of these models. It should be understood that the processes or steps describing the training of these models are performed only once to build and train these models. After the models are built and trained, the training processes as well as the data sets used during the building and training processes are no longer used. Specifically, the training processes as well as the data sets used during the building and training processes are not used during operation, runtime, or production use of the system. Therefore, it should be understood that the training processes are shown and described only for the purpose of explaining how the models are constructed and trained, and are not part of the system when in use. In use, these trained models receive inputs derived from a video being analyzed, and these trained models output data that these models are trained to output based on the inputs received, without again undergoing the model building and training processes during use.

FIG. 1 shows an overall architecture of an automated video analysis system 200 (hereinafter the system 200) of the present disclosure. The system 200 comprises a pre-processing system 202 and a severity scoring system 204. The pre-processing system 202 comprises a source 210 of colonoscopy videos. For example, the source 210 may include a database or an interface capable of receiving, retrieving, or downloading colonoscopy videos, and so on. The pre-processing system 202 further comprises an extractor of frames 212 that extracts frames from the videos, a first model 214 for detecting informative frames from the frames 212, and outputting filtered informative frames 216.

The severity scoring system 204 comprises a disease severity estimator that uses a second model 220 for disease severity estimation, a frame-wise severity estimation 222, and a summary score estimator that uses a third model 224 for summary score estimation. The severity scoring system 204 further comprises a motion-based location classifier that uses a fourth model 230 for motion-based location classification, and an image appearance-based location classifier that uses a fifth model 232 for image appearance-based location classification. The estimated summary score 226 replicates manual endoscopic scoring (the Mayo score). However, the severity scoring system 204 also produces a severity score distribution 236, which is presently not part of the Mayo score. Accordingly, the system 200 generates or provides two outputs—the distribution of scores over the colon segments and a summary score (the Mayo score).

Throughout the present disclosure, references to Models 1-5 should be understood as follows. It should be understood that the informative frame detector 214 uses Model 1 to detect and filter the informative frames. The disease severity estimator 220 uses Model 2 to estimate frame-wise severity scores. The summary score estimator 224 uses Model 3 to estimate the summary score 226. The motion-based location classifier 230 uses Model 4 for motion-based location classification. The image appearance-based location classifier 232 uses Model 5 for image appearance-based location classification.

In the pre-processing system 202, frames are extracted from colonoscopy videos, and non-informative frames are filtered out using an automated informative frame classification model (Models 1, 2, and 3). A disease severity classification model (Model 2) is constructed to estimate a severity score (e.g., a Mayo score) for every informative frame (i.e., frame-wise severity estimation 222). For each colonoscopy video, the output from Model 2 is a sequence of Mayo scores that indicates disease severity throughout the entire colon. A machine learning model (Model 3) extracts features (see FIG. 3 and its description for details) from the sequence of predicted scores and uses them to estimate the summary score for the entire colonoscopy video (i.e., the estimated summary score 226 for the entire colon). The estimated summary scores are compared with scores from human experts to validate the performance of the automated severity scoring system. Additional details of the models are described below with reference to FIGS. 2-5.

Figure 2:
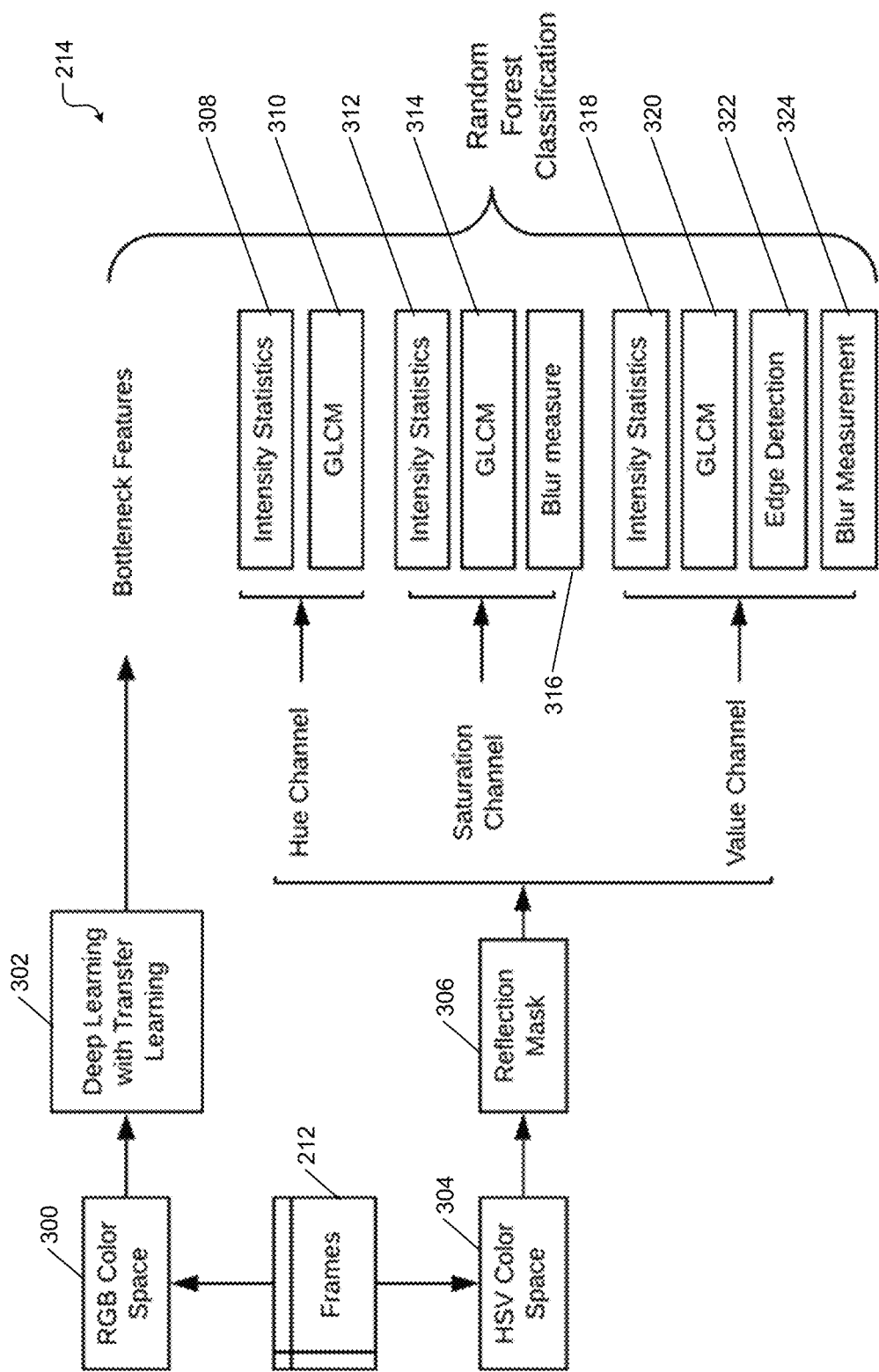
FIG. 2 shows details of a model used in the system of FIG. 1 for detecting informative frames from a colonoscopy video.

FIG. 2 shows an example of the first model (i.e., Model 1—Informative frame detector) 214 in detail. The informative frame detector 214 comprises RGB color space 300, a CNN 302 that is trained using deep learning and transfer learning, HSV color space 304, reflection mask 306, and a group of handcrafted features (defined below) identified at 308 through 324 including intensity statistics, gray-level co-occurrence matrix (GLCM), edges, and blur measurements.

In a colonoscopy video, a large portion of frames 212 are non-informative due to debris such as residual bowel cleansing liquid in the colon (which obscures the field of view of camera), proximity of the camera to the colon wall for inspection, colon surface texture, and blurriness from fast camera motion. These non-informative frames may interrupt disease severity estimation and location estimation by providing non-informative or conflicting information. Removing non-informative frames can reduce computational cost and improve the accuracy of camera motion tracking and disease severity estimation. To distinguish non-informative frames from the informative frames, a random forest classifier is trained using a combination of deep learning and conventional features. An image recognition model (e.g., Inception-v3) along with transfer learning is used to characterize frames in the Red-Green-Blue (RGB) color space; and hand-crafted features including edges, intensity statistics, and the measure of blur and focus are extracted from frames in the Hue-Saturation-Value (HSV) color space. The combination of bottleneck features in the RGB color space and hand-crafted features in the HSV color space improves the classification performance. The informative frame detector 214 uses a combination of bottleneck features from the trained convolutional neural network (CNN) 302 and hand-crafted features 308-324 for informative frame detection as follows.

For a CNN, the last activation (feature) maps before the final fully connected layer in the network (with the fully connected layer being the component that performs the final classification/regression) are used as bottleneck features. The dimension of these feature maps (which are arrays of numbers) is smaller than those in the previous layers, which is why the term bottleneck is used. Accordingly, as used herein, bottleneck features are the last activation feature maps before a final fully connected layer in a CNN, where the final fully connected layer performs final classification or regression. Further, as used herein, hand-crafted features are image processing features (visual and statistical) that are used to identify non-informative frames and to distinguish non-informative frames from informative frames and thus to classify frames as informative versus non-informative.

First, a pre-trained image recognition model (e.g., Inception-v3, not shown) is used to extract textural and high-level features, such as vessel density, (i.e., regions or portions of frames relevant for classifying frames as informative versus non-informative) in the Red-Green-Blue (RGB) color space. Second, hand-crafted features are extracted based on visual information and prior knowledge. In colonoscopy videos, image sharpness can be affected by camera motion. Moreover, image brightness and sharpness are also influenced by variable features in the colon environment including the amount of water or debris present, surface texture, and the distance between the camera and the colon wall. As a result, to better characterize frame contents, frames are converted into the Hue-Saturation-Value (HSV) color space, which can separate color components from the intensity. After conversion, several hand-crafted features such as the measure of edges, blur, and focus are extracted. Finally, the bottleneck features and hand-crafted features are fused and a random forest model is built to classify frames as informative or non-informative. In HSV color space 304, five groups of features including intensity distribution, second order statistics from gray-level co-occurrence matrix (GLCM), edges, reflections and blur measurements are extracted. These features are concatenated with bottleneck features to build the random forest classification model.

To train and test the model, a dataset is built by sampling frames from multiple colonoscopy videos. A board-certified gastroenterologist reviews those frames and manually labels them for frame informativeness.

Figure 3:
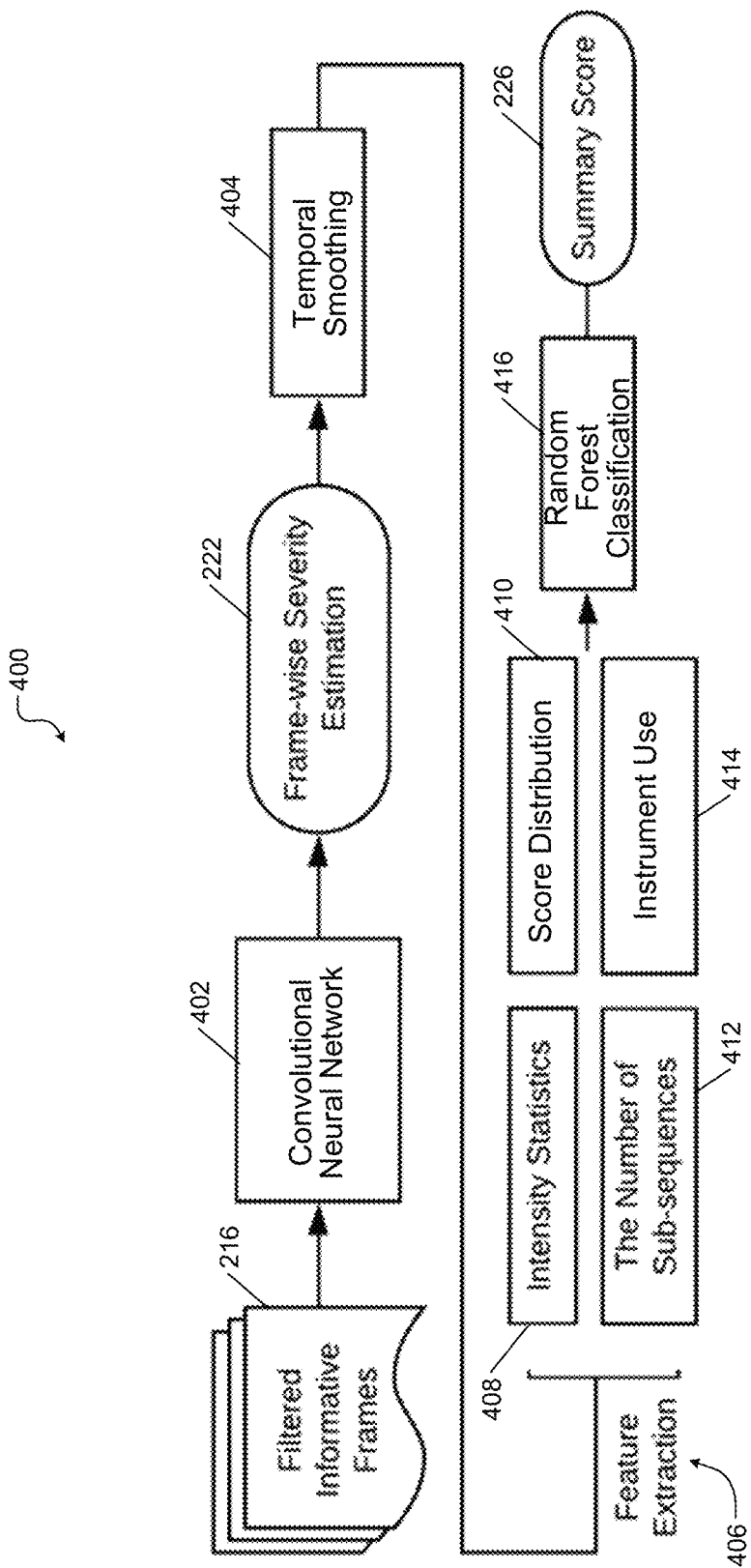
FIG. 3 shows an overall system for severity estimation used in the system of FIG. 1.

FIG. 3 shows an overall system 400 for severity estimation of colonoscopy videos that estimates frame-wise severity scores using the second model (i.e., Model 2 or Disease severity estimator) 220 and that generates summary score 226 using the third model (Model 3 or Summary score estimator) 224. The system 400 comprises a CNN 402, frame-wise severity estimation 222, a temporal smoothing filter 404, feature extraction 406 (examples of features are shown at 408-414), and a random forest model 416. The Model 3 comprises the temporal smoothing filter 404, feature extraction 406 (examples of features are shown at 408-414), and the random forest model 416.

In one embodiment, for disease severity estimation, a relational database is constructed to store metadata related to each colonoscopy video and its component frames, including clinician-generated labels of each frame for disease findings (e.g., polyps) or disease severity features (e.g., ulcerative colitis severity score). These findings and scores are used to train the CNN 402 for automated still image severity estimation. Source images undergo random transformations of rotation, zoom, sheer, and vertical and horizontal orientation to improve the variability of the dataset and prevent overfitting. Transfer learning is used to train a CNN 402 for disease severity estimation, which estimates disease severity in each informative frame detected by Model 1.

More specifically, a relational database is constructed allowing manual import of video, segmentation of videos into individual frames, and manual labeling of each frame for disease findings (e.g., polyps) or disease severity features (e.g., ulcerative colitis severity score). These findings and disease severity grading are then used to train a neural network for automated still image identification. Images are split into a training set (e.g., 80% used for model building and 10% used to tune model hyper-parameters) and a testing set (e.g., 10% are unseen in model development and are used to evaluate final model performance). Source images are downscaled (e.g., to 320×256 resolution) and undergo random transformations of rotation, zoom, sheer, and vertical and horizontal orientation to improve the variability of the dataset and prevent overfitting. Again, the training steps are performed only once and are not performed when the CNN model is used in normal operation to process videos. Once trained, during normal operation, the CNN model outputs a sequence representing the disease severity estimation for each frame.

In an example embodiment, for summary score estimation, each colonoscopy video can be represented using a sequence of estimated scores (e.g., Mayo scores), the length of which is equal to the number of informative frames in that video (example discussed below). Noise within this sequence can be removed using the temporal smoothing filter 404. After de-noising, feature extraction including intensity statistics 408 is performed on the sequence to analyze the distribution of disease severity scores (score distribution 410). Features such as the portion of frames classified as each score class and the number of consecutive sub-sequences 412 in each class are calculated.

The instrument use feature 414 detects whether any tool (e.g., biopsy forceps) or instrument was used during colonoscopy that could cause tissue damage. Tissue damage due to the use of a tool or instrument can be mistaken for active disease and can result in severity misclassification. The instrument use feature 414 is used to distinguish any tissue damage from active disease and to prevent severity misclassification. Finally, a supervised machine learning model (e.g., the random forest model 416) is trained to generate a summary score 226 that indicates the overall disease severity for the colonoscopy video.

After Model 2, the video is transformed into a sequence of numbers, e.g., 00101100000001111212122221110110000. The number of sub-sequences is used as a feature in Model 3 to determine the summary score for the video. This feature (i.e., the number of sub-sequences 412) counts, for each class, the number of sub-sequences of length greater than 1 within the sequence above for each class. For example, in the above string, the number of sub-sequences for class 1 is 4, which are italicized in the above string.

To train and test Model 2 and Model 3, frames from a number of colonoscopy videos are extracted and annotated by gastroenterologists. The gastroenterologists also watch the entire video to evaluate the overall severity (summary score). Clinical trial videos whose summary scores were generated by gastroenterologists are used to validate the model.

The context-sensitive automated scoring system is now described. The overall structure of the context-sensitive automated disease scoring system for colonoscopy videos is shown in FIG. 2 and comprises Models 1, 2, 4, and 5. The system starts with pre-processing colonoscopy videos to determine informative frames (Model 1), and filtered informative frames are input to the severity estimation model (Model 2) to generate frame-wise severity score 222. To better characterize the severity distribution over the colon, frame-wise location estimation is performed in two ways: motion-based (Model 4) and image appearance-based (Model 5), respectively.

In an example embodiment of motion-based location classification (Model 4), first, camera's motion is estimated using pairs of consecutive frames and the optical flow from the frame pairs. The estimation of camera motion enables the reordering of frames with respect to their relative position within the colon. Then the motion-based location classification model operates by building a segmental colon template that represents the relative lengths of colon segments over the entire colon and by assigning accumulated distances traveled to colon segments. The resulting frame-wise localization is further improved by supervised image appearance-based location classification (Model 5) to generate the final location map. With the estimated frame-wise disease grade/severity score from Model 2, the severity score distribution over colon segments can be generated. Additional details of each step are provided below.

In one example embodiment, for motion-based location classification, first, dense optical flow method is applied to generate a vector field indicating pixel-wise motion. Optical flow is a method based on brightness constancy assumption that the brightness of a point remains constant from one frame to the next, even though its position will not. The dense optical flow method is used to generate a pixel-wise motion vector map between frames that are taken at times t and t+Δt. Traditional optical flow methods focus on salient feature extraction and coarse-to-fine framework to search for feature pairs between frames. However, the reliance on accurate image correspondence can cause problems when dealing with colonoscopy videos, wherein areas are of low texture and complex photometry. Instead, an end-to-end CNN model taking advantage of the pyramid structure (i.e., a pyramid shaped view of a portion of colon seen by the camera, see frames shown in FIG. 4) and image warping are used to predict dense optical flow. The calculated optical flow will be used for camera pose estimation.

Figure 4:
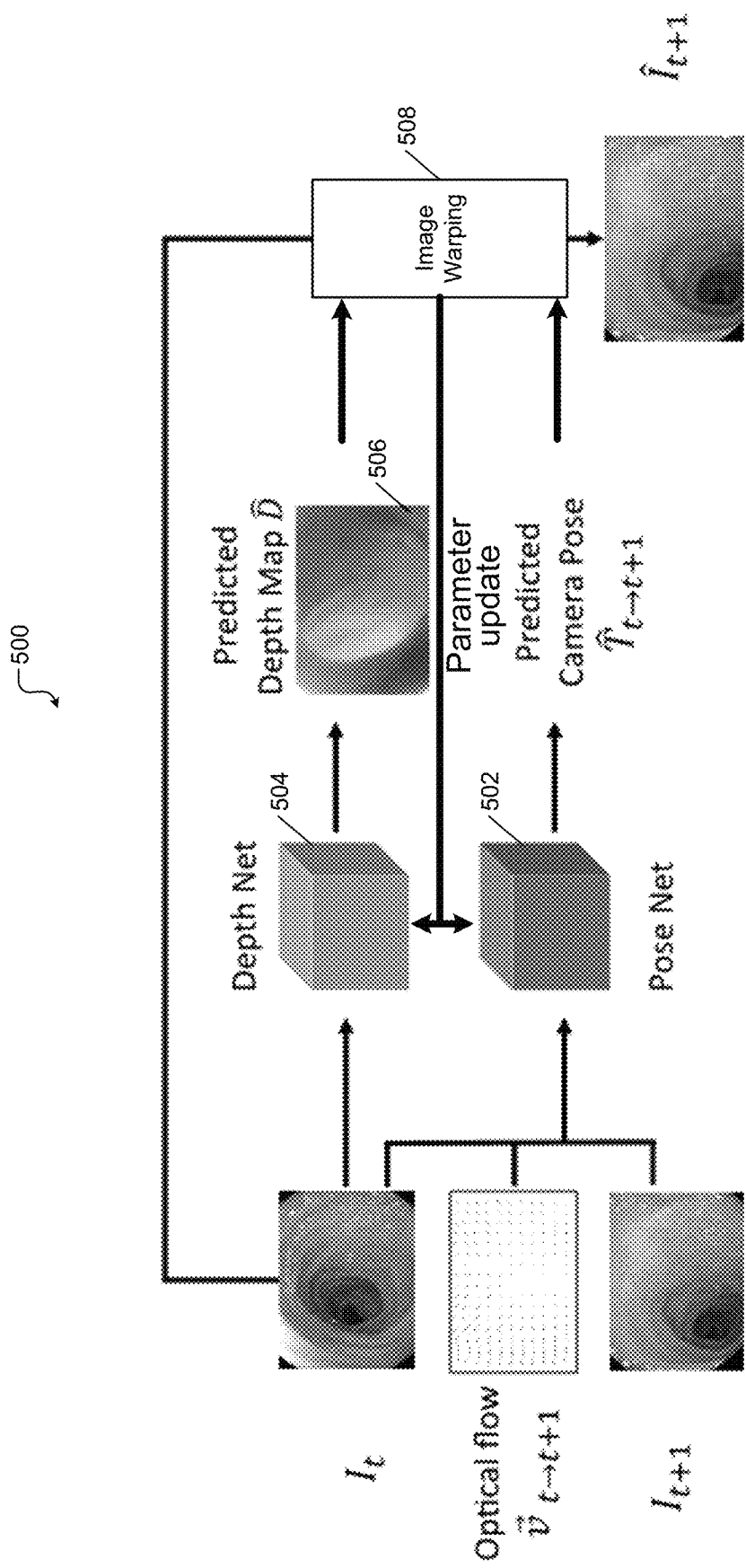
FIG. 4 shows a model used in the system of FIG. 1 for motion-based location estimation.

FIG. 4 shows a camera pose estimation using model 500. The camera motion during colonoscopy is estimated by successively estimating the pose of the camera. Camera pose can be parameterized using the vector $[t_x, t_y, t_z, \theta_x, \theta_y, \theta_z]$, where $t_x, t_y, t_z$ and $\theta_x, \theta_y, \theta_z$ respectively represent three dimensional translation and rotation of the camera. A deep learning-based framework comprising a pose network (PoseNet) 502 and a depth network (DepthNet) 504 is used to estimate camera pose. The input to the framework is a pair of contiguous frames, $I_t$ and $I_{(t+1)}$, as well as the optical flow map between the frame pair $I_t$ and $I_{(t+1)}$. Frame $I_t$ is input into the DepthNet 504 to estimate a depth map 506. In parallel, the pair of frames and the optical flow map is used to estimate the pose of the camera at time t+1, where the camera coordinate frame at the current time t is used as the world coordinate frame. In this way, the camera pose at time point t+1 can be also regarded as the camera motion from t to t+1.

A warping-based image synthesis is used for supervision of the network as follows. Let $p_t$ denote the homogeneous coordinate of a pixel in the frame $I_t$. Using image warping 508, the projected coordinates $p_{(t+1)}$ of $p_t$ at frame $I_{(t+1)}$ can be estimated by:

$$\hat{p}_{t+1} = K\hat{T}_{t\rightarrow t+1}\hat{D}(p_t)K^{-1}p_t,$$

where K is the camera intrinsic matrix, and $\hat{T}_{(t\rightarrow t)}$ and $\hat{D}$ are the predicted camera pose and predicted depth map, respectively. After the projected coordinates of every pixel in frame $I_t$ are calculated, a bilinear interpolation is used to obtain $\hat{I}_{(t+1)}$.

After warping-based image synthesis, a sum of pixel-wise absolute error between $I_{(t+1)}$ and $\hat{I}_{(t+1)}$ is calculated as a loss, and back-propagation is used to update the parameters in the depth network 504 and pose network 502.

By using image synthesis for supervision, no manual annotation is needed to train the network. After the model is trained, frames from new videos are input to the network, and $\hat{T}_{(t\rightarrow t+1)}$ is used to calculate the camera trajectory.

Figure 5:
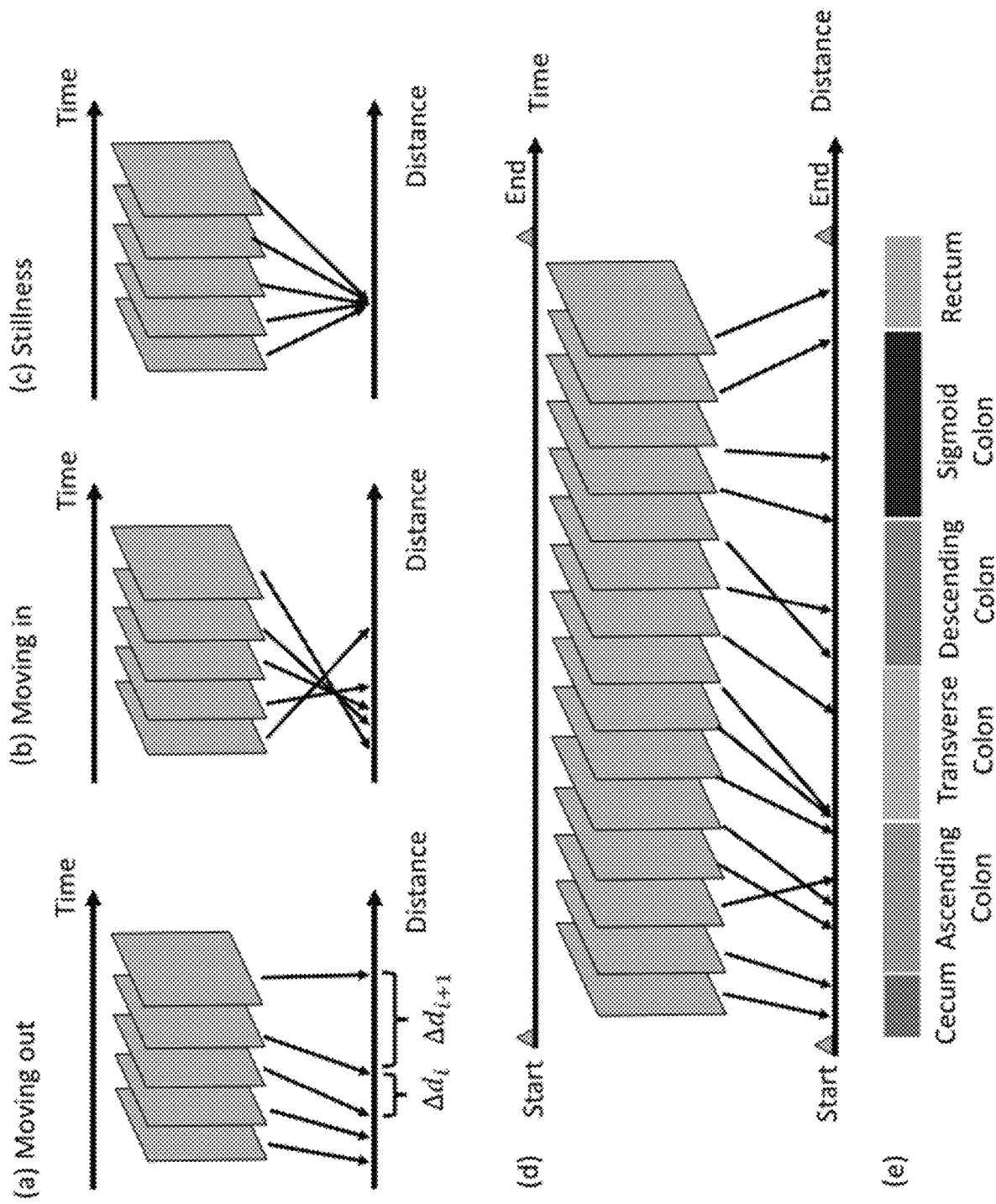
FIG. 5 shows examples of mapping temporal frame indices to distance indices and an example of mapping an entire colonoscopy video.

By successively estimating the pose of the camera using the network shown in FIG. 4, the coordinates of the camera (i.e., camera trajectory) in the world coordinate frame during the colonoscopy are estimated. (A world coordinate system, also called the universe or a model coordinate system, is a base reference system for the overall model to which all other model coordinates relate.) Based on the camera coordinate in the z-axis, frame index t in the temporal domain can be converted to the distance index d. FIG. 5 shows examples of various mappings.

In FIG. 5, items (a)-(c) show examples of mapping temporal frame indices to distance indices under three different motion patterns. Item (d) shows an example of mapping an entire colonoscopy video. Instead of referring to the $i_{th}$ frame at $t_i$ seconds after the withdrawal of the colonoscope, the $i_{th}$ frame can be characterized as the frame $d_i$ centimeters from the beginning of the colon, which is represented as a straight line.

In the training dataset, the times when the colonoscope enters the next colon segment are annotated by a gastroenterologist, who observed the entire colonoscopy video and examines textural characteristics of the colon surface. In one example, six colon segments are considered: the cecum, ascending colon, transverse colon, descending colon, sigmoid colon, and rectum (see FIG. 6). By combining the estimated distance index of each frame and timing annotations, a colon template can be constructed that represents the relative length of each colon segment over the entire colon. As item (e) in FIG. 5 shows, the width of each block (labeled with segment names cecum etc.) indicates the relative length of each colon segment. When new videos are analyzed by the system, motion analysis previously described is first performed to map the video into the distance index. After that, location (i.e., colon segment) classification is performed using the previously created colon template.

An example embodiment of image appearance-based location classification (Model 5) is now described. In different colon segments, the visual features of the colon surface are in general insufficiently distinct to allow for location classification. This limitation is overcome by using Model 4 to generate the overall location classification. However, image appearance and textural features are still useful in two ways. First, they can be used to locate the start (usually at the appendix/cecum) of the withdrawal period. Although the newly published standards for colonoscopy require the recording of the time when colonoscope withdrawal starts, identifying the start point is still essential to make the system applicable to older videos or those from other countries without this standard. Second, the accuracy of motion-based location classification can be impaired if the optical flow and motion analysis fails at a colon segment due to abnormal situations. To improve the robustness of the system, the following image feature-based location classification can provide additional supervision.

Specifically, to find the beginning and end of the withdrawal period, frames in appendix/cecum and rectum need to be identified. A number of images with annotations (appendix, cecum, rectum, others) are used to train a CNN for image appearance-based location classification. The classification of frames into appendix, cecum, and rectum can not only help identify the beginning/end of the withdrawal period, but also provide information for motion tracking. The classification results are integrated into the location map obtained from the camera motion analysis and template matching to improve the accuracy and robustness of motion tracking.

Figure 6:
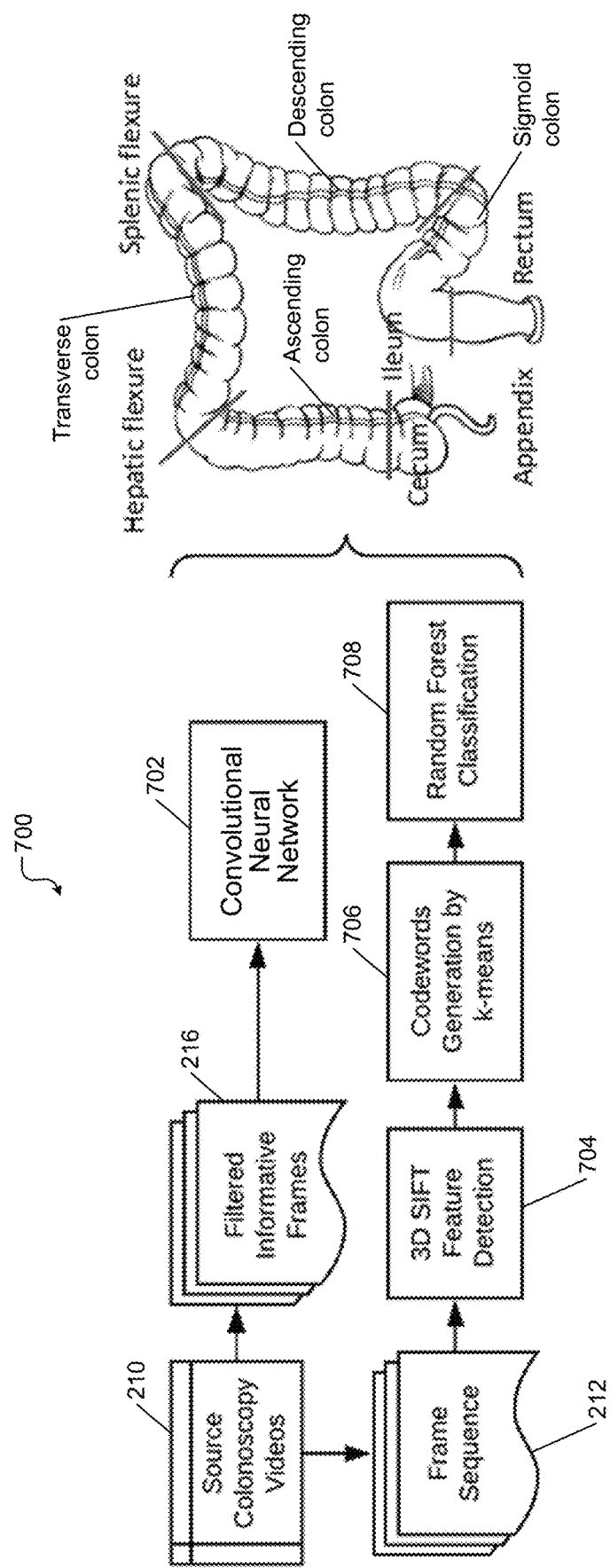
FIG. 6 shows a model used in the system of FIG. 1 for image feature-based location estimation.

FIG. 6 shows a system 700 for image appearance-based location classification (using Model 5). The system 700 comprises a CNN model 702, a 3D SIFT feature detection 704, codeword generation 706, and a random forest classification model 708. Specifically, two classifiers for the system 700 are constructed as follows. First, considering the relatively distinct visual characteristics of the appendix, cecum, rectum, and ileum, a first classifier is constructed to detect frames in these regions. For the training dataset, frames including the four segments appendix, cecum, rectum, or ileum are annotated as such by a gastroenterologist, while frames within other regions are annotated as other frames. The CNN model 702 using an image recognition architecture is built to perform this five-class classification. The input to the CNN model 702 is the filtered informative frames 216 extracted from colonoscopy videos.

A second classifier is built to identify colic flexures. As hepatic flexure and splenic flexure are transitional regions from the ascending colon to the transverse colon, and from the transverse colon to the descending colon, respectively, identifying flexures can effectively help in identifying the current location of the colonoscope in the colon. The camera view in these two flexures is different from other regions (e.g., not a pyramid shape) due to the sharp turns during the camera's motion.

A bag-of-words model is used to detect the flexures. The bag-of-words model is a simplifying representation used in natural language processing and information retrieval. In this model, a text (such as a sentence or a document) is represented as a bag (multiset) of its words, while disregarding grammar and word order but keeping multiplicity.

First, an entire colonoscopy video is divided into a number of frame sequences 212. A 3D scale-invariant feature transform (SIFT) 704 is performed on frame sequences to detect local features. After that, each frame sequence can be represented as a number of variable-length SIFT feature vectors. A k-means algorithm 706 is used to build codewords, which are calculated as the center of observed clusters. A histogram of codewords for each frame sequence is used as features. Finally, a supervised machine learning model (e.g., the random forest classification model) 708 is built to classify whether a frame sequence belongs to a flexure.

The image appearance-based location classification results are integrated into the motion-based location map from Model 4 to improve the accuracy and robustness of the localization system as shown and described above with reference to FIG. 1.

FIG. 7 shows an overall method 800 for automatically analyzing a video recording of a colonoscopy performed on a colon. Further details of the method 800 are shown and described with reference to FIGS. 8-14. The methods shown in FIGS. 7-14 are performed by the system 200 shown in FIG. 1. At 802, control receives a video recording of a colonoscopy. At 804, control detects informative and non-informative frames in the video recording and removes the non-informative frames from the video recording (see FIG. 8 and its description for details of the model used to perform the detection and removal). At 806, control performs frame-wise severity score estimation and generates a score indicating a severity level of a disease for each of the informative frames (see FIG. 9 and its description for details of the model used to perform the frame-wise severity score estimation). At 808, control performs frame-wise location estimation and estimates a location of each of the informative frames in the colon (see FIG. 13 for details and FIGS. 12 and 14 and their description for details of the models used). At 810, control generates an output indicating a distribution of the scores over the colon by combining the scores generated for the informative frames and the estimated locations of the informative frames in the colon (see FIG. 11 for details).

FIG. 8 shows a method 900 for generating a model to automatically detecting informative and non-informative frames in a video recording of a colonoscopy. At 902, the method 900 extracts textural and high level features from the frames of the video recording (i.e., regions or portions of frames relevant for classifying frames as informative versus non-informative) in Red-Green-Blue (RGB) space. At 904, the method 900 obtains bottleneck features from the frames of the video recording in RGB space using deep learning and transfer learning. At 906, the method 900 converts the frames of the video recording from RGB space into Hue-Saturation-Value (HSV) color space. At 908, the method 900 extracts hand-crafted features from the converted frames in HSV color space. At 910, the method 900 builds a frame classification model (e.g., a random forest classifier) using a combination of the bottleneck features and the hand-crafted features to classify (i.e., detect, separate, and/or distinguish) informative and non-informative frames from the frames in the video recording. Subsequently, during use or normal operation, using the frame classification model, the non-informative frames can be removed to facilitate automatic analysis of the informative frames. The method 900 is performed only once to build the frame classification model. The method 900 is not performed during use or normal operation.

Figure 9:
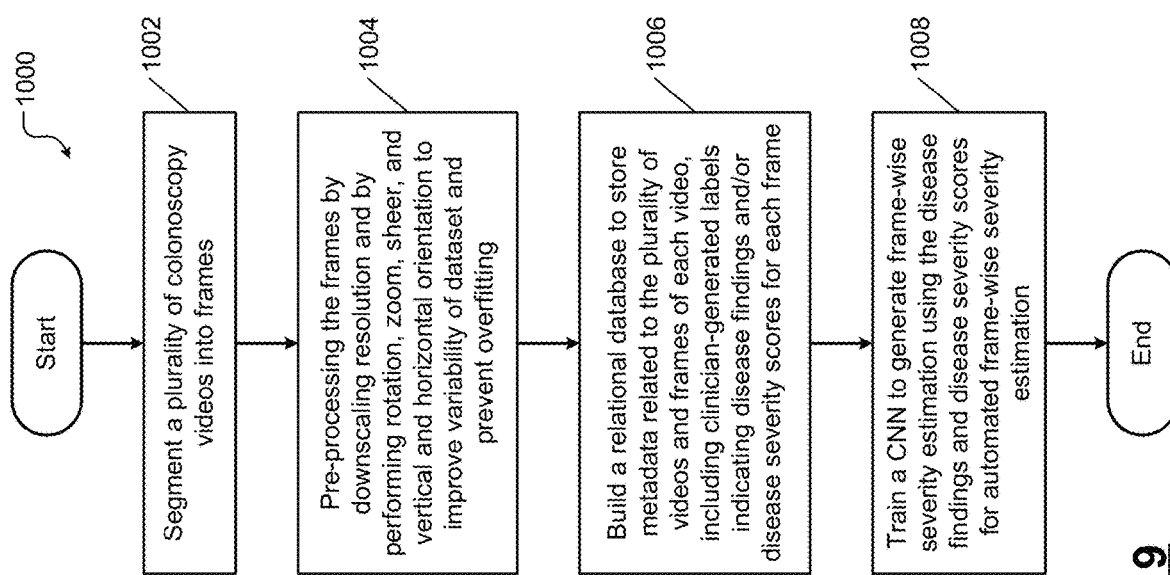
FIG. 9 shows a method for training a model for automatically performing frame-wise severity score estimation for a colonoscopy video according to the present disclosure.

FIG. 9 shows a method 1000 for training a CNN for automatically performing frame-wise severity score estimation for a video recording of a colonoscopy. At 1002, the method 1000 segments a plurality of colonoscopy videos into frames. At 1004, the method 1000 pre-processes the frames by downscaling resolution and by performing rotation, zoom, sheer, and vertical and horizontal orientation to improve variability of data set and prevent overfitting. At 1006, the method 1000 builds a relational database to store metadata related to the plurality of videos and frames of each video, including clinician-generated labels indicating disease findings and/or disease severity scores for each frame indicating severity levels of diseases. At 1008, the method 1000 trains a CNN to generate frame-wise severity estimation using the disease findings and disease severity scores. Subsequently, during use or normal operation, the trained CNN can be used to perform automated frame-wise severity estimation on frames of any other colonoscopy video recordings. The method 1000 is performed only once to train the CNN. The method 1000 is not performed during use or normal operation.

Figure 10:
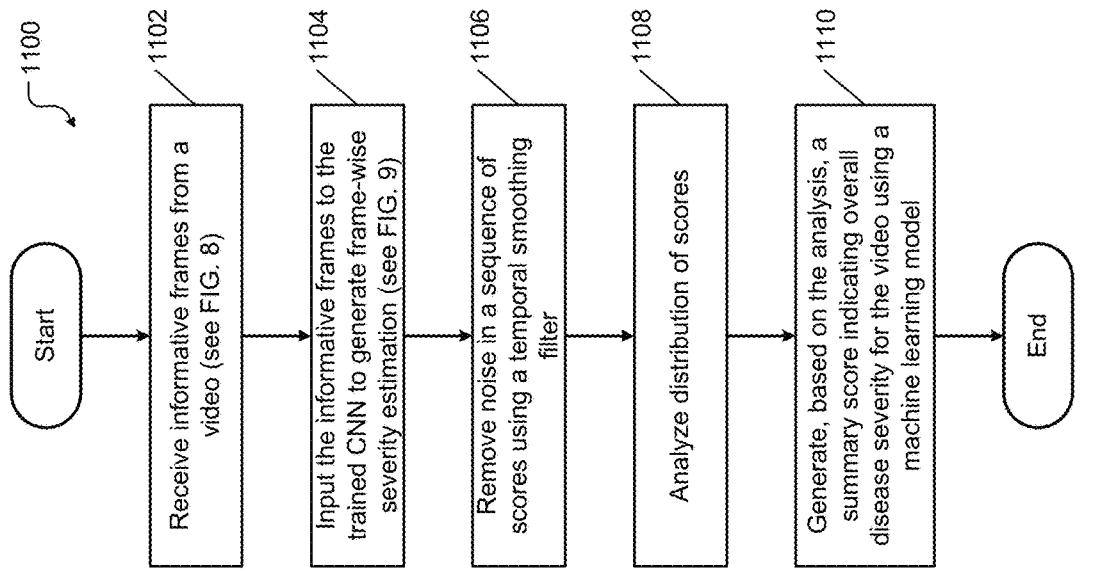
FIG. 10 shows a method for automatically generating a summary score estimation for a colonoscopy video according to the present disclosure.

FIG. 10 shows a method 1100 for automatically generating a summary score estimation for a colonoscopy video recording. At 1102, control receives informative frames from a colonoscopy video recording (see FIG. 8 and its description for details). At 1104, control inputs the informative frames to the trained CNN to generate frame-wise severity estimation (see FIG. 9 and its description for details). At 1106, control removals noise in a sequence of scores using a temporal smoothing filter. At 1108, control analyzes the distribution of the scores. At 1110, control generates, based on the analysis, a summary score indicating overall disease severity for the colonoscopy video recording (i.e., for the entire colon) using a machine learning model.

FIG. 11 shows a method 1200 for automatically performing frame-wise location estimation for a video recording of a colonoscopy. The method 1200 shows an overall method for location estimation. Further details of location estimation are shown and described with reference to FIGS. 12-14. At 1202, control estimates camera motion using pairs of consecutive frames and optical flow from the frame pairs (see FIG. 12 and its description for details for details of the model used). At 1204, control builds a segmental colon template representing relative lengths of colon segments over the entire colon. At 1206, based on the estimated camera motion, using the template, control reorders the frames according to their relative positions within the colon (see FIG. 13 and its description for details). At 1208, control improves frame-wise localization (i.e., frame-wise location estimation) by image appearance-based location classification to generate a final location map (see FIG. 14 and its description for details of the models used). At 1210, using the improved frame-wise location estimation in combination with the estimated frame-wise severity scores (see FIG. 9 and its description for details of the model used), control generates a severity score distribution over the colon segments or the entire colon.

FIG. 12 shows a method 1300 for building a model for automatically estimating camera motion using pairs of consecutive frames and optical flow from the frame pairs of a colonoscopy video recording. At 1302, control builds a deep learning based framework including a pose network and a depth network to estimate camera pose. At 1304, control inputs a pair of contiguous frames (e.g., consecutive or successive frames at times t and t+1) and an optical flow map between the pair of frames to the framework. At 1306, control inputs a first frame (at time t) of the pair of frames to the depth network to estimate a depth map. At 1308, in parallel, control inputs the pair of frames (i.e., both of the contiguous frames) and the optical flow map to the pose network to estimate a pose of the camera at time t+1, which is regarded as the motion of the camera from time t to time t+1. At 1310, control updates the parameters of the depth and pose networks using warping-based image synthesis of the frames.

FIG. 13 shows a method 1400 for automatically mapping frames of a colonoscopy video recording to colon segments. At 1402, control inputs the informative frames extracted from a colonoscopy video recording to trained depth and pose networks (see FIG. 12 and its description for details of the model used). At 1404, control estimates coordinates of the camera (i.e., camera trajectory) by successfully estimating the pose of the camera using the trained depth and pose networks. At 1406, based on the camera coordinates, control converts frame indices in temporal domain into distance indices. At 1408, control maps the temporal frame indices to the distance indices for different camera motions (e.g., forward, backward, and still). At 1410, control maps the temporal frame indices to the distance indices over the colon segments and the entire colon.

FIG. 14 shows a method 1500 for building models for providing image appearance-based location classification for frames of a colonoscopy video recording to generate a final location map. At 1502, the method 1500 builds and trains a CNN to detect frames in four distinct segments of the colon. At 1504, the method 1500 inputs the informative frames to the trained CNN to identify frames in the four colon segments. At 1506, the method 1500 divides the colonoscopy video recording into a number of frame sequences. At 1508, the method 1500 detects local features using 3-D scale invariant feature transform (SIFT). At 1510, the method 1500 builds a machine learning model to classify whether a frame sequence belongs to a flexure of the colon. Subsequently, during use or normal operation, using the two models together, control provides image appearance-based location classification. The method 1500 is performed only once to build and train the two models. The method 1500 is not performed during use or normal operation.

Below are simplistic examples of a distributed computing environment in which the systems and methods of the present disclosure can be implemented. Throughout the description, references to terms such as servers, client devices, applications and so on are for illustrative purposes only. The terms server and client device are to be understood broadly as representing computing devices with one or more processors and memory configured to execute machine readable instructions. The terms application and computer program are to be understood broadly as representing machine readable instructions executable by the computing devices.

Figure 15:
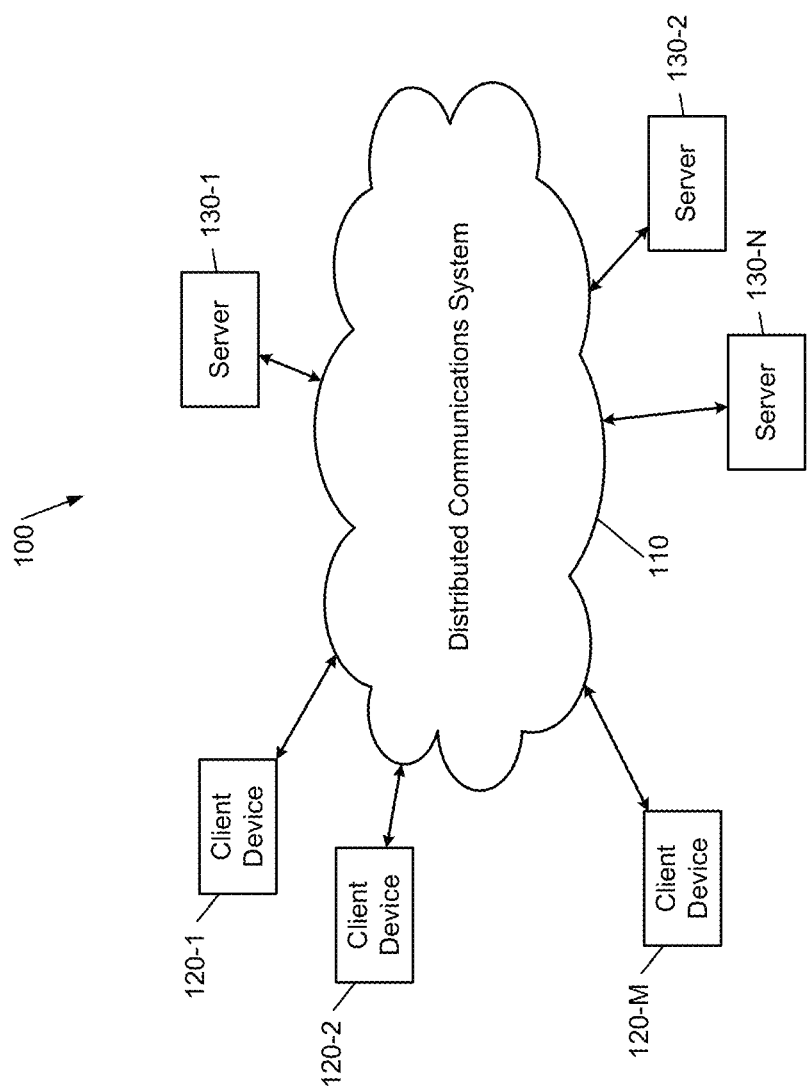
FIG. 15 shows a simplified example of a distributed computing system for implementing the systems and methods of the present disclosure.

FIG. 15 shows a simplified example of a distributed computing system 100. The distributed computing system 100 includes a distributed communications system 110, one or more client devices 120-1, 120-2, . . . , and 120-M (collectively, client devices 120), and one or more servers 130-1, 130-2, . . . , and 130-N (collectively, servers 130). M and N are integers greater than or equal to one. The distributed communications system 110 may include a local area network (LAN), a wide area network (WAN) such as the Internet, or other type of network. The client devices 120 and the servers 130 may be located at different geographical locations and communicate with each other via the distributed communications system 110. The client devices 120 and the servers 130 connect to the distributed communications system 110 using wireless and/or wired connections.

The client devices 120 may include smartphones, personal digital assistants (PDAs), tablets, laptop computers, personal computers (PCs), etc. The servers 130 may provide multiple services to the client devices 120. For example, the servers 130 may execute software applications developed by one or more vendors. The servers 130 may host multiple databases that are relied on by the software applications in providing services to users of the client devices 120. In some examples, one or more of the servers 130 execute one or more applications that implement the systems and methods shown and described above with reference to FIGS. 1-14.

For example, the server 130-1 may execute an application that implements the automated video analysis system of the present disclosure. In some implementations, one or more models (Models 1-5) of the system may be implemented on separate servers or a cluster of servers. For example, the servers 130 may be located in a cloud or on premises. In some examples, a video may be received at one of the servers 130 from one of the client devices 120 (e.g., located at a clinician's office or a hospital) via the distributed communications system 110. After analysis, the results (e.g., score distribution output by the system 10, 200) can be sent to any of the client devices 120. For example, a clinician may send a video to one of the servers 130 for analysis from the client device 120-1 (e.g., a computer in the clinician's office) while the results may be sent to the clinician's mobile phone, which can be another client device, say 120-2. Further, any of the client devices 120 can be provided with a secure access to the system on the server to allow clinicians to download the results from the server to the authorized client device preferred by the clinician.

Figure 16:
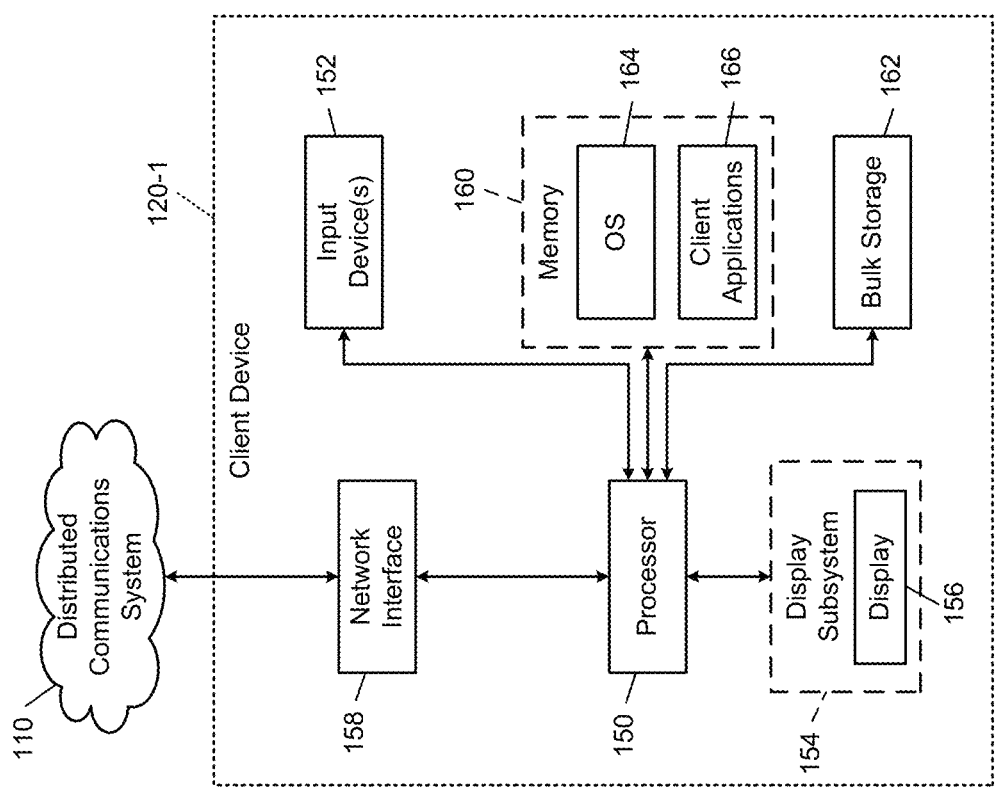
FIG. 16 shows a simplified example of a client device used in the distributed computing system.

FIG. 16 shows a simplified example of the client device 120-1. The client device 120-1 may typically include a central processing unit (CPU) or processor 150, one or more input devices 152 (e.g., a keypad, touchpad, mouse, touchscreen, a colonoscope, etc.), a display subsystem 154 including a display 156, a network interface 158, memory 160, and bulk storage 162.

The network interface 158 connects the client device 120-1 to the distributed computing system 100 via the distributed communications system 110. For example, the network interface 158 may include a wired interface (for example, an Ethernet interface) and/or a wireless interface (for example, a Wi-Fi, Bluetooth, near field communication (NFC), or other wireless interface). The memory 160 may include volatile or nonvolatile memory, cache, or other type of memory. The bulk storage 162 may include flash memory, a magnetic hard disk drive (HDD), and other bulk storage devices.

The processor 150 of the client device 120-1 executes an operating system (OS) 164 and one or more client applications 166. The client applications 166 include an application that accesses the servers 130 via the distributed communications system 110. For example, the client applications 166 can include an application that records a video of colonoscopy performed using a colonoscope, which can be one of the input devices 152 connected to the client device 120-1.

Figure 17:
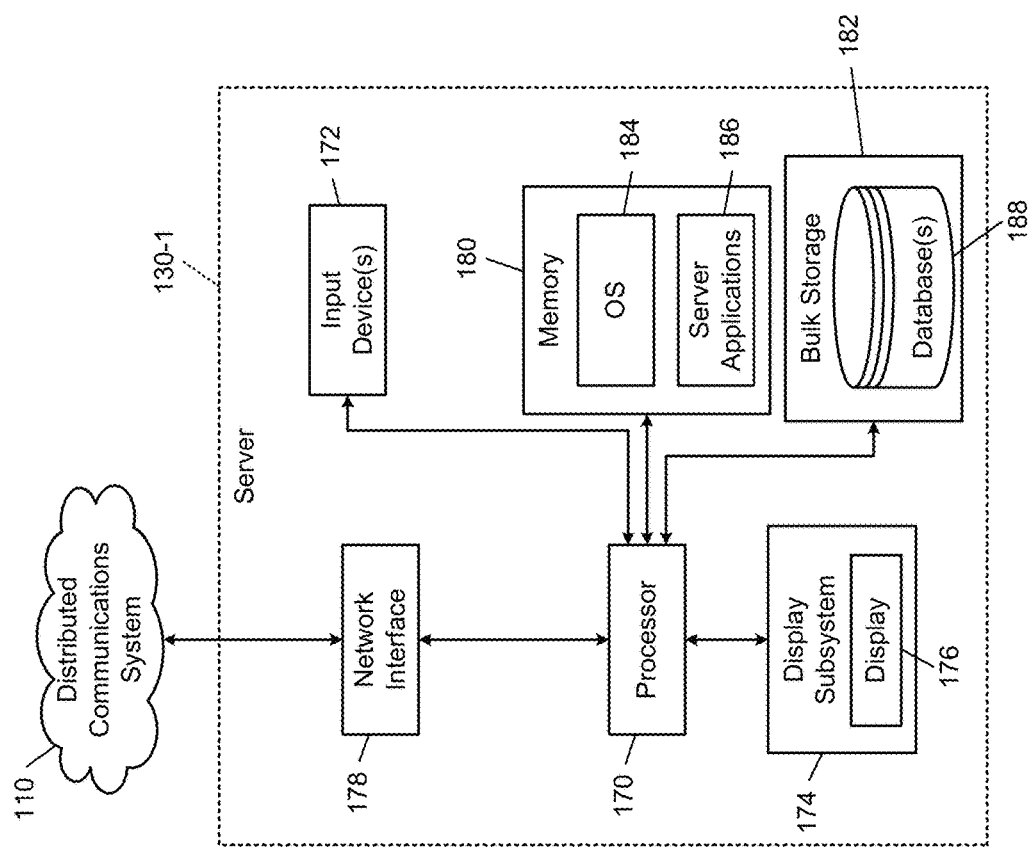
FIG. 17 shows a simplified example of a server used in the distributed computing system.

FIG. 17 shows a simplified example of the server 130-1. The server 130-1 typically includes one or more CPUs or processors 170, a network interface 178, memory 180, and bulk storage 182. In some implementations, the server 130-1 may be a general-purpose server and include one or more input devices 172 (e.g., a keypad, touchpad, mouse, and so on) and a display subsystem 174 including a display 176.

The network interface 178 connects the server 130-1 to the distributed communications system 110. For example, the network interface 178 may include a wired interface (e.g., an Ethernet interface) and/or a wireless interface (e.g., a Wi-Fi, Bluetooth, near field communication (NFC), or other wireless interface). The memory 180 may include volatile or nonvolatile memory, cache, or other type of memory. The bulk storage 182 may include flash memory, one or more magnetic hard disk drives (HDDs), or other bulk storage devices.

The processor 170 of the server 130-1 executes an operating system (OS) 184 and one or more server applications 186, which may be housed in a virtual machine hypervisor or containerized architecture. The bulk storage 182 may store one or more databases 188 that store data structures used by the server applications 186 to perform respective functions. For example, the server applications 186 can implement the video analysis systems and methods shown and described with reference to FIGS. 1-14. Further, any of various components of the system described above may be implemented the server 130-1 and the applications 186.

The foregoing description is merely illustrative in nature and is not intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation) (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

What is claimed is:

1. A system for automatically analyzing a video recording of a colonoscopy performed on a colon, the system comprising:
    a processor; and
    memory storing instructions, which when executed by the processor, cause the processor to:
        receive the video recording of the colonoscopy performed on the colon;
        detect informative frames in the video recording, wherein a frame is informative if the clarity of the frame is above a threshold or if the frame includes clinically relevant information about the colon;
        generate scores indicating severity levels of a disease for a plurality of the informative frames;
        estimate locations of the plurality of the informative frames in the colon; and
        generate an output indicating a distribution of the scores over one or more segments of the colon by combining the scores generated for the plurality of the informative frames and the estimated locations of the plurality of the informative frames in the colon.

2. The system of claim 1 wherein the instructions cause the processor to generate a summary score based on the scores generated for the plurality of the informative frames and wherein the summary score indicates an overall disease severity for the colon.

3. The system of claim 1 wherein the instructions cause the processor to:
    input frames of the video recording to a frame classification model to identify non-informative frames and to distinguish the non-informative frames from the informative frames; and
    receive the informative frames from the frames in the video recording from the frame classification model.

4. The system of claim 1 wherein the instructions cause the processor to:
    extract features from frames of the video recording used for classifying frames as informative versus non-informative in Red-Green-Blue color space;
    input the features to a convolutional neural network;
    receive, from the convolutional neural network, bottleneck features from the frames of the video recording in Red-Green-Blue color space;
    convert the frames of the video recording into Hue-Saturation-Value color space;
    extract other features from the converted frames to identify non-informative frames and to distinguish the non-informative frames from the informative frames; and
    generate a frame classification model using a combination of the bottleneck features and the other features to identify the non-informative frames and to distinguish the non-informative frames from the informative frames.

5. The system of claim 1 wherein the instructions cause the processor to:
    input the plurality of the informative frames to a convolutional neural network to receive the scores for the plurality of the informative frames; and
    receive the scores for the plurality of the informative frames from the convolutional neural network.

6. The system of claim 1 wherein the instructions cause the processor to:
    generate a relational database to store metadata including disease findings and scores indicating severity levels of diseases from frames of a plurality of video recordings of colonoscopies; and
    generate a convolutional neural network using the metadata and the frames to output the scores for the plurality of the informative frames.

7. The system of claim 1 wherein the instructions cause the processor to:
    remove noise from the scores generated for the plurality of the informative frames using a temporal smoothing filter, wherein the scores include a sequence of numbers;
    analyze the distribution of the scores;
    obtain, based on the analysis, features including a number of sub-sequences of length greater than one in the sequence of numbers per score class;
    input the features to a machine learning model; and
    receive, from the machine learning model, a summary score indicating an overall disease severity for the colon.

8. The system of claim 1 wherein the instructions cause the processor to estimate the locations of the plurality of the informative frames in the colon by:
    estimating motion of a camera used to capture the video recording based on pairs of frames from the plurality of the informative frames and optical flow from the pairs of frames;
    generating a template representing relative lengths of segments of the colon;
    determining, using the template, relative positions of the plurality of the informative frames in the segments of the colon based on the estimated motion of the camera; and
    reordering the plurality of the informative frames according to the relative positions of the plurality of the informative frames in the segments of the colon.

9. The system of claim 8 wherein the instructions cause the processor to refine the estimates of the locations of the plurality of the informative frames in the colon by:
    identifying frames from the plurality of the informative frames including distinctive features belonging to selected ones of the segments of the colon; and
    identifying frames from the plurality of the informative frames including distinctive features belonging to flexures of the colon.

10. The system of claim 1 wherein the instructions cause the processor to:
generate a deep learning network to estimate a pose of a camera used to capture the video recording, wherein the deep learning network includes a depth network to predict a depth map of the colon visible to the camera and a pose network to predict the pose of the camera;
input a first frame taken at a first time to the depth network;
input a second frame taken at a second time and an optical flow map between the first and second frames to the pose network, wherein the second time is successive to the first time; and
determine the pose of the camera at the second time based on the depth map and the pose predicted respectively by the depth and pose networks, wherein the pose of the camera at the second time indicates a motion of the camera from the first time to the second time.

11. The system of claim 10 wherein the instructions cause the processor to update parameters of the depth and pose networks based on a warping-based image synthesis of the first frame.

12. The system of claim 1 wherein the instructions cause the processor to:
input two consecutive frames from the plurality of the informative frames to a deep learning network to estimate a pose of a camera used to capture the video recording, wherein the deep learning network includes a depth network to predict a depth map of the colon visible to the camera and a pose network to predict the pose of the camera;
receive coordinates of the camera by successively estimating the pose of the camera from the deep learning network;
convert, based on the coordinates, temporal indices of the two consecutive frames into distance indices; and
map, based on the distance indices, the two consecutive frames to one or more segments of the colon.

13. The system of claim 1 wherein the instructions cause the processor to:
input the plurality of the informative frames to a first model to detect frames including distinctive features belonging to selected segments of the colon;
receive, from the first model, frames from the plurality of the informative frames including the distinctive features belonging to the selected segments of the colon;
divide the video recording into a plurality of frame sequences;
detect features of the colon in the frame sequences;
generate a second model to determine, based on the detected features, whether one or more of the frame sequences belong to a flexure of the colon;
input the frame sequences to the second model; and
receive, from the second model, frames from the plurality of the informative frames belonging to a flexure of the colon.

14. A system for automatically analyzing a video recording of a colonoscopy performed on a colon, the system comprising:
a processor; and
memory storing instructions, which when executed by the processor, cause the processor to:
receive the video recording of the colonoscopy performed on the colon;
extract features from frames of the video recording used for classifying frames as informative versus non-informative in Red-Green-Blue color space;
input the features to a convolutional neural network;
receive, from the convolutional neural network, bottleneck features from the frames of the video recording in Red-Green-Blue color space;
convert the frames of the video recording into Hue-Saturation-Value color space;
extract other features from the converted frames to identify non-informative frames and to distinguish the non-informative frames from the informative frames, wherein a frame is informative if the clarity of the frame is above a threshold or if the frame includes clinically relevant information about the colon; and
generate a frame classification model using a combination of the bottleneck features and the other features to automatically identify the non-informative frames and output the informative frames.

15. The system of claim 14 wherein the instructions cause the processor to:
generate scores indicating severity levels of a disease for a plurality of the informative frames;
estimate locations of the plurality of the informative frames in the colon; and
generate an output indicating a distribution of the scores over one or more segments of the colon by combining the scores generated for the plurality of the informative frames and the estimated locations of the plurality of the informative frames in the colon.

16. The system of claim 15 wherein the instructions cause the processor to generate a summary score based on the scores generated for the plurality of the informative frames and wherein the summary score indicates an overall disease severity for the colon.

17. The system of claim 15 wherein the instructions cause the processor to:
input the plurality of the informative frames to a convolutional neural network to receive the scores for the plurality of the informative frames; and
receive the scores for the plurality of the informative frames from the convolutional neural network.

18. The system of claim 15 wherein the instructions cause the processor to:
generate a relational database to store metadata including disease findings and scores indicating severity levels of diseases from frames of a plurality of video recordings of colonoscopies; and
generate a convolutional neural network using the metadata and the frames to output the scores for the plurality of the informative frames.

19. The system of claim 15 wherein the instructions cause the processor to:
remove noise from the scores generated for the plurality of the informative frames using a temporal smoothing filter, wherein the scores include a sequence of numbers;
analyze the distribution of the scores;
obtain, based on the analysis, features including a number of sub-sequences of length greater than one in the sequence of numbers per score class;
input the features to a machine learning model; and
receive, from the machine learning model, a summary score indicating an overall disease severity for the colon.

20. The system of claim 15 wherein the instructions cause the processor to estimate the locations of the plurality of the informative frames in the colon by:

estimating motion of a camera used to capture the video recording based on pairs of frames from the plurality of the informative frames and optical flow from the pairs of frames;
generating a template representing relative lengths of segments of the colon;
determining, using the template, relative positions of the plurality of the informative frames in the segments of the colon based on the estimated motion of the camera; and
reordering the plurality of the informative frames according to the relative positions of the plurality of the informative frames in the segments of the colon.

21. The system of claim 20 wherein the instructions cause the processor to refine the estimates of the locations of the informative frames in the colon by:
identifying frames from the plurality of the informative frames including distinctive features belonging to selected ones of the segments of the colon; and
identifying frames from the plurality of the informative frames including distinctive features belonging to flexures of the colon.

22. The system of claim 14 wherein the instructions cause the processor to:
generate a deep learning network to estimate a pose of a camera used to capture the video recording, wherein the deep learning network includes a depth network to predict a depth map of the colon visible to the camera and a pose network to predict the pose of the camera;
input a first frame taken at a first time to the depth network;
input a second frame taken at a second time and an optical flow map between the first and second frames to the pose network, wherein the second time is successive to the first time; and
determine the pose of the camera at the second time based on the depth map and the pose predicted respectively by the depth and pose networks, wherein the pose of the camera at the second time indicates a motion of the camera from the first time to the second time.

23. The system of claim 22 wherein the instructions cause the processor to update parameters of the depth and pose networks based on a warping-based image synthesis of the first frame.

24. The system of claim 14 wherein the instructions cause the processor to:
input two consecutive frames from the plurality of the informative frames to a deep learning network to estimate a pose of a camera used to capture the video recording, wherein the deep learning network includes a depth network to predict a depth map of the colon visible to the camera and a pose network to predict the pose of the camera;
receive coordinates of the camera by successively estimating the pose of the camera from the deep learning network;
convert, based on the coordinates, temporal indices of the two consecutive frames into distance indices; and
map, based on the distance indices, the two consecutive frames to one or more segments of the colon.

25. The system of claim 14 wherein the instructions cause the processor to:
input the plurality of the informative frames to a first model to detect frames including distinctive features belonging to selected segments of the colon;
receive, from the first model, frames from the plurality of the informative frames including the distinctive features belonging to the selected segments of the colon;
divide the video recording into a plurality of frame sequences;
detect features of the colon in the frame sequences;
generate a second model to determine, based on the detected features, whether one or more of the frame sequences belong to a flexure of the colon;
input the frame sequences to the second model; and
receive, from the second model, frames from the plurality of the informative frames belonging to a flexure of the colon.

26. A system for automatically analyzing a video recording of a colonoscopy performed on a colon, the system comprising:
a processor; and
memory storing instructions, which when executed by the processor, cause the processor to:
receive the video recording of the colonoscopy performed on the colon;
detect informative frames in the video recording, wherein a frame is informative if the clarity of the frame is above a threshold or if the frame includes clinically relevant information about the colon;
input the plurality of the informative frames to a convolutional neural network; and
receive scores indicating severity levels of a disease for the plurality of the informative frames from the convolutional neural network.

27. The system of claim 26 wherein the instructions cause the processor to:
generate a relational database to store metadata including disease findings and scores indicating severity levels of diseases from frames of a plurality of video recordings of colonoscopies; and
generate a convolutional neural network using the metadata and the frames to output the scores for the plurality of the informative frames.

28. The system of claim 26 wherein the instructions cause the processor to generate a summary score based on the scores generated for the plurality of the informative frames and wherein the summary score indicates an overall disease severity for the colon.

29. The system of claim 26 wherein the instructions cause the processor to:
estimate locations of the plurality of the informative frames in the colon; and
generate an output indicating a distribution of the scores over one or more segments of the colon by combining the scores generated for the plurality of the informative frames and the estimated locations of the plurality of the informative frames in the colon.

30. The system of claim 26 wherein the instructions cause the processor to:
input frames of the video recording to a frame classification model to identify non-informative frames and to distinguish the non-informative frames from the informative frames; and
receive the informative frames from the frames in the video recording from the frame classification model.

31. The system of claim 26 wherein the instructions cause the processor to:
extract features from frames of the video recording used for classifying frames as informative versus non-informative in Red-Green-Blue color space;
input the features to a convolutional neural network;

receive, from the convolutional neural network, bottleneck features from the frames of the video recording in Red-Green-Blue color space;
convert the frames of the video recording into Hue-Saturation-Value color space;
extract other features from the converted frames to identify non-informative frames and to distinguish the non-informative frames from the informative frames; and
generate a frame classification model using a combination of the bottleneck features and the other features to identify the non-informative frames and to distinguish the non-informative frames from the informative frames.

32. The system of claim 29 wherein the instructions cause the processor to:
input the plurality of the informative frames to a convolutional neural network to receive the scores for the plurality of the informative frames; and
receive the scores for the plurality of the informative frames from the convolutional network.

33. The system of claim 29 wherein the instructions cause the processor to estimate the locations of the plurality of the informative frames in the colon by:
estimating motion of a camera used to capture the video recording based on pairs of frames from the plurality of the informative frames and optical flow from the pairs of frames;
generating a template representing relative lengths of segments of the colon;
determining, using the template, relative positions of the plurality of the informative frames in the segments of the colon based on the estimated motion of the camera; and
reordering the plurality of the informative frames according to the relative positions of the plurality of the informative frames in the segments of the colon.

34. The system of claim 33 wherein the instructions cause the processor to refine the estimates of the locations of the plurality of the informative frames in the colon by:
identifying frames from the plurality of the informative frames including distinctive features belonging to selected ones of the segments of the colon; and
identifying frames from the plurality of the informative frames including distinctive features belonging to flexures of the colon.

35. The system of claim 26 wherein the instructions cause the processor to:
generate a deep learning network to estimate a pose of a camera used to capture the video recording, wherein the deep learning network includes a depth network to predict a depth map of the colon visible to the camera and a pose network to predict the pose of the camera;
input a first frame taken at a first time to the depth network;
input a second frame taken at a second time and an optical flow map between the first and second frames to the pose network, wherein the second time is successive to the first time; and
determine the pose of the camera at the second time based on the depth map and the pose predicted respectively by the depth and pose networks, wherein the pose of the camera at the second time indicates a motion of the camera from the first time to the second time.

36. The system of claim 35 wherein the instructions cause the processor to update parameters of the depth and pose networks based on a warping-based image synthesis of the first frame.

37. The system of claim 26 wherein the instructions cause the processor to:
input two consecutive frames from the plurality of the informative frames to a deep learning network to estimate a pose of a camera used to capture the video recording, wherein the deep learning network includes a depth network to predict a depth map of the colon visible to the camera and a pose network to predict the pose of the camera;
receive coordinates of the camera by successively estimating the pose of the camera from the deep learning network;
convert, based on the coordinates, temporal indices of the two consecutive frames into distance indices; and
map, based on the distance indices, the two consecutive frames to one or more segments of the colon.

38. The system of claim 26 wherein the instructions cause the processor to:
input the plurality of the informative frames to a first model to detect frames including distinctive features belonging to selected segments of the colon;
receive, from the first model, frames from the plurality of the informative frames including the distinctive features belonging to the selected segments of the colon;
divide the video recording into a plurality of frame sequences;
detect features of the colon in the frame sequences;
generate a second model to determine, based on the detected features, whether one or more of the frame sequences belong to a flexure of the colon;
input the frame sequences to the second model; and
receive, from the second model, frames from the plurality of the informative frames belonging to a flexure of the colon.

39. A system for automatically analyzing a video recording of a colonoscopy performed on a colon, the system comprising:
a processor; and
memory storing instructions, which when executed by the processor, cause the processor to:
receive the video recording of the colonoscopy performed on the colon;
detect informative frames in the video recording, wherein a frame is informative if the clarity of the frame is above a threshold or if the frame includes clinically relevant information about the colon; and
estimate locations of a plurality of the informative frames in the colon by:
estimating motion of a camera used to capture the video recording based on pairs of frames from the plurality of the informative frames and optical flow from the pairs of frames;
generating a template representing relative lengths of segments of the colon;
determining, using the template, relative positions of the plurality of the informative frames in the segments of the colon based on the estimated motion of the camera; and
reordering the plurality of the informative frames according to the relative positions of the plurality of the informative frames in the segments of the colon.

40. The system of claim 39 wherein the instructions cause the processor to:
  generate scores indicating severity levels of a disease for the plurality of the informative frames; and
  generate an output indicating a distribution of the scores over one or more segments of the colon by combining the scores generated for the plurality of the informative frames and the estimated locations of the plurality of the informative frames in the colon.

41. The system of claim 40 wherein the instructions cause the processor to generate a summary score based on the scores generated for the plurality of the informative frames and wherein the summary score indicates an overall disease severity for the colon.

42. The system of claim 39 wherein the instructions cause the processor to:
  input frames of the video recording to a frame classification model to identify non-informative frames and to distinguish the non-informative frames from the informative frames; and
  receive the informative frames from the frames in the video recording from the frame classification model.

43. The system of claim 39 wherein the instructions cause the processor to:
  extract features from frames of the video recording used for classifying frames as informative versus non-informative in Red-Green-Blue color space;
  input the features to a convolutional neural network;
  receive, from the convolutional neural network, bottleneck features from the frames of the video recording in Red-Green-Blue color space;
  convert the frames of the video recording into Hue-Saturation-Value color space;
  extract other features from the converted frames to identify non-informative frames and to distinguish the non-informative frames from the informative frames; and
  generate a frame classification model using a combination of the bottleneck features and the other features to identify the non-informative frames and to distinguish the non-informative frames from the informative frames.

44. The system of claim 40 wherein the instructions cause the processor to:
  input the plurality of the informative frames to a convolutional neural network to receive the scores for the plurality of the informative frames; and
  receive the scores for the plurality of the informative frames from the convolutional neural network.

45. The system of claim 39 wherein the instructions cause the processor to:
  generate a relational database to store metadata including disease findings and scores indicating severity levels of diseases from frames of a plurality of video recordings of colonoscopies; and
  generate a convolutional neural network using the metadata and the frames to output scores for the plurality of the informative frames.

46. The system of claim 40 wherein the instructions cause the processor to:
  remove noise from the scores generated for the plurality of the informative frames using a temporal smoothing filter, wherein the scores include a sequence of numbers;
  analyze the distribution of the scores;
  obtain, based on the analysis, features including a number of sub-sequences of length greater than one in the sequence of numbers per score class;
  input the features to a machine learning model; and
  receive, from the machine learning model, a summary score indicating an overall disease severity for the colon.

47. The system of claim 39 wherein the instructions cause the processor to refine the estimates of the locations of the informative frames in the colon by:
  identifying frames from the plurality of the informative frames including distinctive features belonging to selected ones of the segments of the colon; and
  identifying frames from the plurality of the informative frames including distinctive features belonging to flexures of the colon.

48. The system of claim 39 wherein the instructions cause the processor to:
  generate a deep learning network to estimate a pose of a camera used to capture the video recording, wherein the deep learning network includes a depth network to predict a depth map of the colon visible to the camera and a pose network to predict the pose of the camera;
  input a first frame taken at a first time to the depth network;
  input a second frame taken at a second time and an optical flow map between the first and second frames to the pose network, wherein the second time is successive to the first time; and
  determine the pose of the camera at the second time based on the depth map and the pose predicted respectively by the depth and pose networks, wherein the pose of the camera at the second time indicates a motion of the camera from the first time to the second time.

49. The system of claim 48 wherein the instructions cause the processor to update parameters of the depth and pose networks based on a warping-based image synthesis of the first frame.

50. The system of claim 39 wherein the instructions cause the processor to:
  input two consecutive frames from the plurality of the informative frames to a deep learning network to estimate a pose of a camera used to capture the video recording, wherein the deep learning network includes a depth network to predict a depth map of the colon visible to the camera and a pose network to predict the pose of the camera;
  receive coordinates of the camera by successively estimating the pose of the camera from the deep learning network;
  convert, based on the coordinates, temporal indices of the two consecutive frames into distance indices; and
  map, based on the distance indices, the two consecutive frames to one or more segments of the colon.

51. The system of claim 39 wherein the instructions cause the processor to:
  input the plurality of the informative frames to a first model to detect frames including distinctive features belonging to selected segments of the colon;
  receive, from the first model, frames from the plurality of the informative frames including the distinctive features belonging to the selected segments of the colon;
  divide the video recording into a plurality of frame sequences;
  detect features of the colon in the frame sequences;

generate a second model to determine, based on the detected features, whether one or more of the frame sequences belong to a flexure of the colon;
input the frame sequences to the second model; and
receive, from the second model, frames from the plurality of the informative frames belonging to a flexure of the colon.

* * * * *